(12) United States Patent
Pain et al.

(10) Patent No.: US 7,786,121 B2
(45) Date of Patent: Aug. 31, 2010

(54) DERIVATIVES OF HYDROXAMIC ACID AS METALLOPROTEINASE INHIBITORS

(75) Inventors: Gilles Pain, Bresso (IT); Stephen John Davies, Abingdon (GB); Agnes Bombrun, Chambesy (CH)

(73) Assignees: Vernalis (Oxford) Limited (GB); Laboratoires Serono S.A. (CH)

(*) Notice: Subject to any disclaimer, the term of this patent is extended or adjusted under 35 U.S.C. 154(b) by 100 days.

(21) Appl. No.: 10/568,433

(22) PCT Filed: Aug. 18, 2004

(86) PCT No.: PCT/GB2004/003558

§ 371 (c)(1),
(2), (4) Date: Aug. 8, 2006

(87) PCT Pub. No.: WO2005/019194

PCT Pub. Date: Mar. 3, 2005

(65) Prior Publication Data

US 2006/0281920 A1 Dec. 14, 2006

(30) Foreign Application Priority Data

Aug. 23, 2003 (GB) ................. 0319917.1
Dec. 10, 2003 (GB) ................. 0328632.5

(51) Int. Cl.
*A61K 31/497* (2006.01)
*C07D 241/04* (2006.01)
*C07D 295/00* (2006.01)

(52) U.S. Cl. ................. 514/252.12; 544/358

(58) Field of Classification Search .................. None
See application file for complete search history.

(56) References Cited

U.S. PATENT DOCUMENTS 5,703,092 A 12/1997 Xue et al.
5,917,090 A 6/1999 Spavold et al.
2008/0021028 A1* 1/2008 Swinnen et al. .......... 514/235.8

FOREIGN PATENT DOCUMENTS

| EP | 0 684 240 A | 11/1995 |
| WO | WO 99/44989 A1 | 9/1999 |
| WO | WO 01/44179 A1 | 6/2001 |
| WO | WO 02/102791 A1 | 12/2002 |
| WO | WO 03/070711 A | 8/2003 |

OTHER PUBLICATIONS

Roach, H. Expert Opinion in Drug Disocovery, 2008, 3(5), 475-86.*
"Osteoarthritis Prevention—WebMD", http://www.webmd.com/osteoarthritis/tc/osteoarthritis-prevention, accessed May 5, 2008.*
"Arthritis Prevention", http://www.symptomsofarthritis.com/arthritis-Prevention.html, accessed May 5, 2008.*
Vippagunta et al. Advanced Drug Delivery Reviews, 2001, 48, 3-26.*
Clark et al. Expert Opinion in Therapeutic Targets, 2003, 7(1), 19-34.*
"Prophylaxis definition", http://www.medterms.com/script/main/art.asp?articlekey=12063, accessed Feb. 12, 2009.*
Wermuth. The Practice of Medicinal Chemistry, 1996, pp. 203-237.*

* cited by examiner

*Primary Examiner*—James O Wilson
*Assistant Examiner*—Noble Jarrell
(74) *Attorney, Agent, or Firm*—Banner & Witcoff, Ltd.

(57) ABSTRACT

A compound of formula (I), or an enantiomer or diastereoisomer thereof, or a salt, hydrate or solvate thereof:

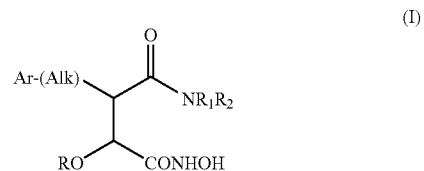

for the treatment or prophylaxis of arthritis in mammals.

19 Claims, No Drawings

DERIVATIVES OF HYDROXAMIC ACID AS METALLOPROTEINASE INHIBITORS

This application is a U.S. National Stage application of co-pending PCT application PCT/GB2004/003558, filed Aug. 18, 2004, which claims the priority of Great Britain Patent Application No. 0319917.1, filed Aug. 23, 2003, and Great Britain Patent Application No. 0328632.5, filed Dec. 10, 2003. These applications are incorporated herein by reference in their entireties.

The present invention relates to therapeutically active hydroxamic acid derivatives, to processes for their preparation, to pharmaceutical compositions containing them, and to the use of such compounds in medicine. In particular, the compounds are inhibitors of matrix metalloproteinases.

BACKGROUND TO THE INVENTION

The matrix metalloproteinases (MMP's) are a family of zinc containing endopeptidases which are capable of cleaving large biomolecules such as the collagens, proteoglycans and gelatins. Imbalance between active MMPs and endogenous inhibitors, leads to excessive tissue disruption. The three main groups of MMPs are the collagenases, the gelatinases, and the stromelysins. Collagenases include fibroblast collagenase (MMP-1), neutrophil collagenase (MMP-8), and collagenase 3 (MMP-13). Gelatinases include 72 kDa gelatinase (gelatinase A; MMP-2) and 92 kDa gelatinase (gelatinase B; MMP-9). Stromelysins include stromelysin 1 (MMP-3), stromelysin 2 (MMP-10) and matrilysin (MMP-7). However there are MMPs which do not fit neatly into the above groups, for example metalloelastase (MMP-12), membrane-type MMP (MT-MMP or MMP-14) and stromelysin 3 (MMP-11).

Over-expression and activation of MMPs have been linked with a wide range of diseases such as cancer; rheumatoid arthritis; osteoarthritis; chronic inflammatory disorders, such as asthma, bronchitis and emphysema; cardiovascular disorders, such as atherosclerosis; corneal ulceration; dental diseases such as gingivitis and periodontal disease; neurological disorders, such as multiple sclerosis and restenosis. For example, MMP-12 is required for the development of cigarette smoke-induced emphysema in mice, Science, 277, 2002 (1997). Inhibition of MMPs is therefore a strategy for treatment of such disease states. However, there is evidence that non-selective inhibition of matrix metalloproteinase activity may affect normal physiological process leading to dose limiting side effects. Selective inhibition of MMP-12 and/or MMP-9 is thought to be a particularly relevant strategy for intervention in inflammatory conditions.

Some MMPs can hydrolyse the membrane-bound precursor of the pro-inflammatory cytokine tumour necrosis factor α: (TNF-α). This cleavage yields mature soluble TNF-α and some inhibitors of MMPs can block production of TNF-α both in vitro and in vivo. This pharmacological action is a probable contributor to the anti-inflammatory action of this class of compounds.

For a recent review of MMP inhibition as reflected in the patent literature, see Doherty et. al. Therapeutic Developments in Matrix Metalloproteinase Inhibition; Expert Opinions on Therapeutic Patents, 2002, 12, 665-707.

Very many of the MMP inhibitors of the prior art have a hydroxamic acid metal binding group (—CONHOH).

BRIEF DESCRIPTION OF THE INVENTION

The present invention provides a class of compounds which in general are selective inhibitors of MMP-12 relative to the collagenases and stromelysins. In addition, compounds of the invention can exhibit selective activity towards MMP-9. Compounds of the invention are therefore indicated for treatment of diseases primarily mediated by MMP-12 and/or MMP-9, especially inflammatory conditions such as multiple sclerosis and fibrosis.

DETAILED DESCRIPTION OF THE INVENTION

According to the invention, there is provided a compound of formula (I), or an enantiomer or diastereoisomer thereof, or a salt, hydrate or solvate thereof:

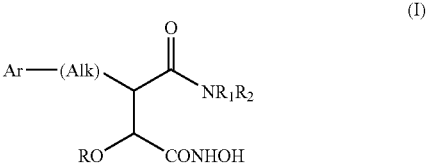

(I)

wherein
Ar represents an optionally substituted aryl, heteroaryl, $C_3$-$C_8$ cycloalkyl or heterocycloakyl group;
R represents hydrogen or $C_1$-$C_6$ alkyl, or $C_3$-$C_6$ cycloalkyl;
Alk represents a divalent $C_1$-$C_5$ alkylene or $C_2$-$C_5$ alkenylene radical; and
$R_1$ and $R_2$ taken together with the nitrogen atom to which they are attached form a first heterocycloalkyl ring which is optionally fused to a second $C_3$-$C_8$ cycloalkyl or heterocycloalkyl ring, the said first and second rings being optionally substituted by a at least one group of formula (II):

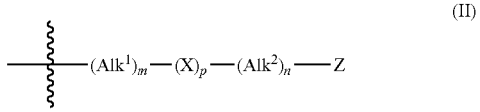

(II)

wherein
m, p and n are independently 0 or 1;
Z represents, hydrogen, or an optionally substituted carbocyclic or heterocyclic ring of from 5 to 7 ring atoms which is optionally fused to another optionally substituted carbocyclic or heterocyclic ring of from 5 to 7 ring atoms;
$Alk^1$ and $Alk^2$ independently represent optionally substituted divalent $C_1$-$C_3$ alkylene radicals;
X represents —O—, —S—, —S(O)—, —S(O$_2$)—, —C(=O)—, —NH—, —NR$_3$—, —S(O$_2$)NH—, —S(O$_2$)NR$_3$—, —NHS(O$_2$)—, or —NR$_3$S(O$_2$)—, where $R_3$ is $C_1$-$C_3$ alkyl.

As used herein the term "($C_a$-$C_b$)alkyl" where a and b are integers refers to a straight or branched chain alkyl moiety having from a to b carbon atoms, including for example, methyl, ethyl, n-propyl, isopropyl, n-butyl, isobutyl, sec-butyl, n-pentyl and n-hexyl, depending on the values of a and b.

As used herein the term "divalent ($C_a$-$C_b$)alkylene radical" where a and b are integers refers to a saturated hydrocarbon chain having from a to b carbon atoms and two unsatisfied valences.

As used herein the term "($C_a$-$C_b$)alkenyl" where a and b are integers refers to a straight or branched chain alkenyl moiety having from a to b carbon atoms having at least one double bond of either E or Z stereochemistry where applicable. The term includes, for example, vinyl, allyl, 1- and 2-butenyl and 2-methyl-2-propenyl, depending on the values of a and b.

As used herein the term "divalent $(C_a-C_b)$alkenylene radical" refers to a hydrocarbon chain having from a to b carbon atoms, at least one double bond, and two unsatisfied valences.

As used herein the unqualified term "carbocyclyl" or "carbocyclic" refers to a ring or ring system of from 3 to 14 ring atoms which are all carbon, and includes "aryl", "cycloalkyl", and "cycloalkenyl" as defined below.

As used herein the unqualified term "cycloalkyl" refers to a saturated alicyclic moiety having from 3-8 carbon atoms consisting of a single ring (e.g. cyclohexyl) or multiple condensed rings (e.g. norbornyl). Preferred cycloalkyl include cyclopentyl, cyclohexyl, norbornyl and the like.

As used herein the unqualified term "cycloalkenyl" refers to an unsaturated alicyclic moiety having from 3-8 carbon atoms and includes, for example, cyclopropenyl, cyclobutenyl, cyclopentenyl, cyclohexenyl, cycloheptenyl and cyclooctenyl. In the case of cycloalkenyl rings of from 5-8 carbon atoms, the ring may contain more than one double bond.

As used herein the unqualified term "aryl" refers to an aromatic carbocyclic group of from 6 to 14 carbon atoms having a single ring or multiple condensed rings and to two covalently linked monocyclic carbocyclic aromatic groups. Examples of aryl include phenyl, biphenyl and the like.

As used herein the unqualified term "heterocyclyl" or "heterocyclic" refers to a ring or ring system whose ring members include one or more hetero atoms selected from O, S, and N, and the term includes "heteroaryl" and "heterocycloalkyl" as defined below.

As used herein, the unqualified term "heterocycloalkyl" refers to a cycloaklyl group as defined above, in which up to 3 ring carbon atoms are replaced by heteroatoms selected from O, S and N. Preferred heterocycloalkyl include pyrrolidine, piperidine, piperazine, 1-methyl piperazine, morpholine, and the like.

As used herein the unqualified term "heteroaryl" refers to a monocyclic, or fused bicyclic or tricyclic aromatic ring or ring system containing one or more heteroatoms selected from O, S and N, and to groups consisting of two covalently linked monocyclic aromatic rings containing one or more such heteroatoms; and to groups consisting of a monocyclic carbocyclic aromatic group covalently linked to monocyclic aromatic ring containing one or more heteroatoms. Particular examples of heteroaromatic groups include optionally substituted pyridyl, pyrimidinyl, pyrrolyl, furyl, thienyl, thiophenyl, imidazolyl, oxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,2,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo [1,2,-c]pyridyl, benzothiazolyl, benzoxazolyl, quinazolyl, quinazolinyl, phthalazinyl, quinoxalinyl, cinnolyl, naphthyridinyl, pyrido[3,4-c]pyridyl, pyrido[3,2-c]pyridyl, pyrido[3,4,3-c]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

Unless otherwise specified in the context in which it occurs, the term "substituted" as applied to any moiety herein means substituted, for example, with at least one substituent selected from $(C_1-C_6)$alkyl, $(C_1-C_6)$alkoxy, hydroxy, hydroxy$(C_1-C_6)$alkyl, mercapto, mercapto$(C_1-C_6)$alkyl, $(C_1-C_6)$alkylthio, halo (including fluoro and chloro), trifluoromethyl, trifluoromethoxy, nitro, nitrile (—CN), oxo, phenyl, —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NHCOOR$^A$, —NR$^B$COOR$^A$, —NHSO$_2$OR$^A$, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$ or —NR$^A$CONR$^A$R$^B$ wherein R$^A$ and R$^B$ are independently a $(C_1-C_6)$alkyl or phenyl group.

As used herein the term "salt" includes base addition, acid addition and quaternary salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris (hydroxymethyl)amino-methane, L-arginine, L-lysine, N-ethyl piperidine, dibenzylamine and the like. Those compounds (I) which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesunfonic, glutamic, lactic, and mandelic acids and the like.

For a review on suitable salts, see *Handbook of Pharmaceutical Salts: Properties, Selection, and Use* by Stahl and Wermuth (Wiley-VCH, Weinheim, Germany, 2002).

The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Compounds with which the invention is concerned which may exist in one or more stereoisomeric form, because of the presence of asymmetric atoms or rotational restrictions, can exist as a number of stereoisomers with R or S stereochemistry at each chiral centre or as atropisomeres with R or S stereochemistry at each chiral axis. The invention includes all such enantiomers and diastereoisomers and mixtures thereof. In particular the invention includes compounds having the stereochemical configuration (IA):

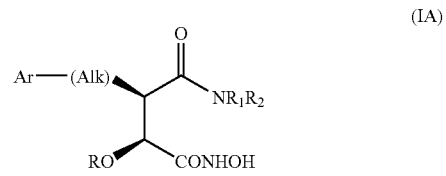

(IA)

The compounds of the invention include compounds of formula (I) as hereinbefore defined, including all polymorphs and crystal habits thereof, prodrugs and isomers thereof (including optical, geometric and tautomeric isomers) as hereinafter defined and isotopically-labeled compounds of formula (I).

The Group Ar

Ar may be, for example, a 5- or 6-membered monocyclic aryl or heteroaryl ring, which is optionally substituted, for example in the 4-position in the case of a 6-membered ring, or in the 2- and/or 3-position in the case of a 5-membered ring, by at least one substituent selected from $(C_1-C_3)$alkyl, $(C_1-C_3)$alkoxy, hydroxy, hydroxy$(C_1-C_3)$alkyl, mercapto, mercapto$(C_1-C_3)$alkyl, $(C_1-C_3)$alkylthio, halo, trifluoromethyl, trifluoromethoxy, nitro, nitrile (—CN), —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NHCOOR$^A$, —NR$^B$COOR$^A$, —NHSO$_2$OR$^A$, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$, or —NR$^A$CONR$^A$R$^B$ wherein R$^A$ and R$^B$ are independently C$_1$-C$_3$ alkyl, phenyl or a 5- or 6-membered monocyclic aryl or heteroaryl ring.

Ar may be, for example phenyl, 2-, 3-, or 4-pyridyl, 2-, or 3-thienyl, or 2-, or 3-furanyl, optionally substituted as specified above in relation to formula (I). Preferably the substituent can be, for example, methoxy, ethoxy, trifluoromethoxy, methyl, ethyl, trifluoromethyl, hydroxyl, mercapto, fluoro, chloro, or bromo. Presently it is preferred that Ar be 4-(C$_1$-C$_3$alkoxy)phenyl, and the most preferred being the ethoxyphenyl.

The Group R

In one embodiment of the invention R is hydrogen.

In another embodiment of the invention R is (C$_1$-C$_6$)alkyl, for example ethyl, n-propyl, isopropyl, n-, sec or tert-butyl. In a preferred embodiment, R is methyl.

In yet another embodiment R is C$_3$-C$_6$ cycloalkyl, for example cyclopropyl, or cyclopentyl.

The Alk Radical

Alk may be, for example, —CH$_2$—, —CH$_2$CH$_2$—, —CH$_2$CH(CH$_3$)—, —CH$_2$CH$_2$CH$_2$—, —CH$_2$CH$_2$CH$_2$CH$_2$—, —CH═CH—, —CH$_2$CH═CH—, —CH$_2$CH═CHCH$_2$—, or —CH═CHCH═CH—. Presently it is preferred that Alk be —CH$_2$CH$_2$CH$_2$—.

The Group —NR$_1$R$_2$

This group is a saturated heterocyclic first ring of 5 to 7 atoms which is optionally fused to a saturated or unsaturated carbocyclic or heterocyclic second ring of 5 to 7 atoms. (The said first and/or second ring may optionally be substituted by a group of formula (II), discussed below). One of the heteroatoms of the group —NR$_1$R$_2$ is of course the nitrogen shown, and it may be the sole heteroatom in the ring system of there may be other nitrogen, oxygen or sulphur ring atoms.

The group —NR$_1$R$_2$ may be unsubstituted or substituted by at least one group (II):

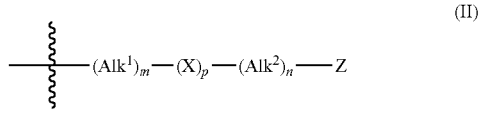
(II)

It will be noted that since an optional substituent in either Alk$^1$ or Alk$^1$ may be oxo, a carbonyl group may be located adjacent the X element, forming for example combinations such as amide, reverse amide and carboxy linkages.

In one embodiment of the invention, R$_1$ and R$_2$ taken together with the nitrogen atom to which they are attached form a morpholyl group, optionally substituted by at least one group of formula (II).

In another embodiment of the invention, R$_1$ and R$_2$ taken together with the nitrogen atom to which they are attached form a thiomorpholyl group, optionally substituted by at least one group of formula (II).

In another embodiment of the invention, R$_1$ and R$_2$ taken together with the nitrogen atom to which they are attached form a piperidinyl group, optionally substituted by at least one group of formula (II).

In another embodiment of the invention, R$_1$ and R$_2$ taken together with the nitrogen atom to which they are attached form a pyrrolidinyl group, optionally substituted by at least one group of formula (II).

In another embodiment of the invention, R$_1$ and R$_2$ taken together with the nitrogen atom to which they are attached form a piperazinyl group, optionally substituted by at least one group of formula (II).

In one particular embodiment of the invention, group (II) is such that p is 0, Z is hydrogen and at least one of n and m is 1. In this subclass the group (II) is optionally substituted C$_1$-C$_6$ alkyl, which may be linked to a ring carbon or to a ring nitrogen of the —NR$_1$R$_2$ group. For example when —NR$_1$R$_2$ is piperidinyl or piperazinyl, the 4-C (in the former) and the 4-N (in the latter) may be substituted by methyl, ethyl, or n- or iso-propyl.

In a second particular embodiment of the invention, group (II) is such that m, n and p are all 0 and Z is a carbocyclic or heterocyclic ring directly linked to a ring carbon or ring nitrogen of the —NR$_1$R$_2$ group. Examples of such directly linked rings Z include cyclopentyl and cyclohexyl, and (preferably) aryl or heteroaryl rings such as phenyl, pyridyl, thienyl, furanyl, and pyrimidinyl.

These directly linked rings may themselves be substituted by optional substituents, for example methoxy, ethoxy, n- or iso-propoxy, trifluoromethoxy, methylenedioxy, ethylenedioxy, methyl, ethyl, n- or isopropyl, trifluoromethyl, fluoro, chloro, bromo, methylsulfonyl, phenylsulfonyl, or mono- or di-(C$_1$-C$_3$)alkylamino.

In a third particular embodiment of the invention, group (II) is such that p is 0, at least one of m and n is 1, and Z is a carbocyclic or heterocyclic ring linked to a ring carbon or ring nitrogen of the —NR$_1$R$_2$ group via a C$_1$-C$_6$ alkylene linker between Z and the —NR$_1$R$_2$ ring. In this case, the ring Z may be any of those optionally substituted Z rings discussed and preferred above in the case of the second subclass of groups (II), but here Z is linked to the —NR$_1$R$_2$ ring via an optionally substituted C$_1$-C$_6$ alkylene linker radical, such as a —CH$_2$— or —CH$_2$CH$_2$— radical.

In a fourth particular embodiment of the invention, group (II) is such that p is 1, so that the group (II) contains the X heteroatom. Clearly when m is 0, X is directly linked to the —NR$_1$R$_2$ ring; when m and n are both 1 X interrupts a C$_1$-C$_6$ alkylene linker between Z and the —NR$_1$R$_2$ ring; and when one of m and n is 1 and the other 0, the group (II) represents a variety of O, S— or N containing substituents either directly linked to the —NR$_1$R$_2$ ring, or linked via a C$_1$-C$_3$alkylene linker.

A particular embodiment of the invention comprises compounds of formula (IB) or (IC) and salts, hydrates and solvates thereof, especially compounds having the stereoconfiguration shown in formula (IA above):

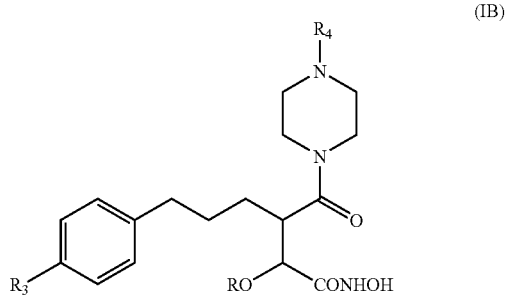
(IB)

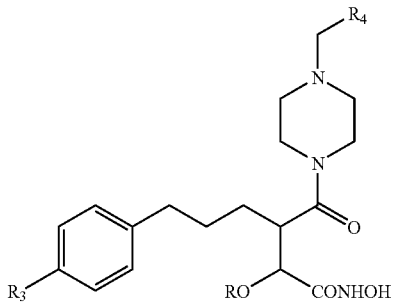
(IC)

wherein R is hydrogen or methyl, $R_3$ is trifluoromethyl, trifluoromethoxy $C_1$-$C_3$alkoxy, hydroxy, or halo; $R_4$ is (i) —$SO_2R_5$ or —$COR_5$ wherein $R_5$ is $C_1$-$C_6$alkyl or phenyl or monocyclic heteroaryl having 5 or 6 ring atoms, optionally substituted by ($C_1$-$C_3$)alkyl, ($C_1$-$C_3$)alkoxy, hydroxy, hydroxy($C_1$-$C_3$)alkyl, mercapto, mercapto($C_1$-$C_3$)alkyl, ($C_1$-$C_3$)alkylthio, halo, trifluoromethyl, trifluoromethoxy or (ii) phenyl or monocyclic heteroaryl having 5 or 6 ring atoms; optionally substituted by ($C_1$-$C_3$)alkyl, ($C_1$-$C_3$)alkoxy, hydroxy, hydroxy($C_1$-$C_3$)alkyl, mercapto, mercapto($C_1$-$C_3$) alkyl, ($C_1$-$C_3$)alkylthio, halo, trifluoromethyl, trifluoromethoxy). Examples of heteroaryl rings forming part of $R_4$ in this embodiment include pyridyl, pyrimidinyl, triazinyl, thienyl, and furanyl.

Specific embodiments of the invention are compounds selected from the group consisting of the following:

6-(4-ethoxy-phenyl)-2S-hydroxy-3R-(pyrrolidine-1-carbonyl)-hexanoic acid hydroxyamide.
3R-(6,7-dimethoxy-3,4-dihydro-1H-isoquinoline-2-carbonyl)-6-(4-ethoxy-phenyl)-2S-hydroxy-hexanoic acid hydroxyamide.
6-(4-ethoxy-phenyl)-2S-hydroxy-3R-[4-(3-methoxy-phenyl)-piperazine-1-carbonyl]-hexanoic acid hydroxyamide.
6-(4-ethoxy-phenyl)-2S-hydroxy-3R-[4-(4-methoxy-phenyl)-piperazine-1-carbonyl]-hexanoic acid hydroxyamide.
6-(4-ethoxy-phenyl)-2S-hydroxy-3R-(4-pyridin-2-yl-piperazine-1-carbonyl)-hexanoic acid hydroxyamide.
6-(4-ethoxy-phenyl)-2S-hydroxy-3R-(4-pyridin-4-yl-piperazine-1-carbonyl)-hexanoic acid hydroxyamide.
6-(4-ethoxy-phenyl)-2S-hydroxy-3R-(morpholine-4-carbonyl)-hexanoic acid hydroxyamide.
6-(4-ethoxy-phenyl)-2S-hydroxy-3R-(2RS-methyl-morpholine-4-carbonyl)-hexanoic acid hydroxyamide.
6-(4-ethoxy-phenyl)-2S-hydroxy-3R-(2,6-RS-dimethyl-morpholine-4-carbonyl)-hexanoic acid hydroxyamide.
6-(4-ethoxy-phenyl)-2S-hydroxy-3R-(thiomorpholine-4-carbonyl)-hexanoic acid hydroxyamide.
3R-(4-benzyl-piperidine-1-carbonyl)-6-(4-ethoxy-phenyl)-2S-hydroxy-hexanoic acid hydroxyamide.
3R-(4-benzo[1,3]dioxol-5-ylmethyl-piperazine-1-carbonyl)-6-(4-ethoxy-phenyl)-2S-hydroxy-hexanoic acid hydroxyamide.
6-(4-ethoxy-phenyl)-2S-hydroxy-3R-(4-pyridin-4-ylmethyl-piperazine-1-carbonyl)-hexanoic acid hydroxyamide.
6-(4-ethoxy-phenyl)-2S-hydroxy-3R-(4-benzylpiperazine-1-carbonyl)-hexanoic acid hydroxyamide.
6-(4-ethoxy-phenyl)-2S-hydroxy-3R-(4-pyrimidin-2-yl-piperazine-1-carbonyl)-hexanoic acid hydroxyamide.
6-(4-ethoxy-phenyl)-2S-hydroxy-3R-[4-(4-trifluoromethyl-pyrimidin-2-yl)-piperazine-1-carbonyl]-hexanoic acid hydroxyamide.
6-(4-ethoxy-phenyl)-2S-hydroxy-3R-[4-(4-chloro-pyrimidin-2-yl)-piperazine-1-carbonyl]-hexanoic acid hydroxyamide.
3R-[4-(4,6-dimethoxy-[1,3,5]triazin-2-yl)-piperazine-1-carbonyl]-6-(4-ethoxy-phenyl)-2S-hydroxy-hexanoic acid hydroxyamide.
6-(4-ethoxy-phenyl)-2S-hydroxy-3R-[4-(3-trifluoromethyl-phenyl)-piperazine-1-carbonyl]-hexanoic acid hydroxyamide.
6-(4-ethoxy-phenyl)-2S-hydroxy-3R-[4-(2-fluoro-phenyl)-piperazine-1-carbonyl]-hexanoic acid hydroxyamide.
3R-[4-(acetyl-methyl-amino)-piperidine-1-carbonyl]-6-(4-ethoxy-phenyl)-2S-hydroxy-hexanoic acid hydroxyamide.
6-(4-ethoxy-phenyl)-2S-hydroxy-3R-[4-(methyl-propyl-amino)-piperidine-1-carbonyl]-hexanoic acid hydroxyamide.
6-(4-ethoxy-phenyl)-2S-hydroxy-3R-(3S-benzyl-morpholine-4-carbonyl)-hexanoic acid hydroxyamide.
6-(4-ethoxy-phenyl)-2S-hydroxy-3R-(3S-isobutyl-morpholine-4-carbonyl)-hexanoic acid hydroxyamide.
6-(4-ethoxy-phenyl)-2S-hydroxy-3R-(3S-phenyl-morpholine-4-carbonyl)-hexanoic acid hydroxyamide.
3R-(4-benzyl-3RS-methyl-piperazine-1-carbonyl)-6-(4-ethoxy-phenyl)-2S-hydroxy-hexanoic acid hydroxyamide.
3R-(3S,4-dibenzyl-piperazine-1-carbonyl)-6-(4-ethoxy-phenyl)-2S-hydroxy-hexanoic acid hydroxyamide.
3R-(4-benzyl-3RS-phenyl-piperazine-1-carbonyl)-6-(4-ethoxy-phenyl)-2S-hydroxy-hexanoic acid hydroxyamide.
4-(4-benzo[1,3]dioxol-5-ylmethyl-piperazin-1-yl)-2S,N-dihydroxy-4-oxo-3R-(4-trifluoromethoxy-benzyl)-butyramide.
3R-benzyl-2S,N-dihydroxy-4-morpholin-4-yl-4-oxo-butyramide.
3R-(4-Benzyloxy-benzyl)-2S,N-dihydroxy-4-oxo-4-piperidin-1-yl-butyramide.
2S,N-dihydroxy-3R-(4-hydroxy-benzyl)-4-oxo-4-piperidin-1-yl-butyramide.
4-(4-benzo[1,3]dioxol-5-ylmethyl-piperazin-1-yl)-3R-(4-benzyloxy-benzyl)-2S,N-dihydroxy-4-oxo-butyramide.
6-(3,5-bis-trifluoromethyl-phenyl)-2S-hydroxy-3R-(morpholine-4-carbonyl)-hexanoic acid hydroxyamide.
3R-(4-benzyl-piperidine-1-carbonyl)-6-(3,5-bis-trifluoromethyl-phenyl)-2S-hydroxy-hexanoic acid hydroxyamide.
6-(3,5-bis-trifluoromethyl-phenyl)-2S-hydroxy-3R-(4-pyridin-2-yl-piperazine-1-carbonyl)-hexanoic acid hydroxyamide.
6-(3,5-bis-trifluoromethyl-phenyl)-3R-(6,7-dimethoxy-3,4-dihydro-1H-isoquinoline-2-carbonyl)-2S-hydroxy-hexanoic acid hydroxyamide.
6-(3,5-bis-trifluoromethyl-phenyl)-2S-hydroxy-3R-(pyrrolidine-1-carbonyl)-hexanoic acid hydroxyamide
3R-(2S-benzyl-4-methyl-piperazine-1-carbonyl)-6-(4-ethoxy-phenyl)-2S-hydroxy-hexanoic acid hydroxyamide.
6-(4-ethoxy-phenyl)-2S-hydroxy-3R-[4-(4-trifluoromethyl-benzenesulfonyl)-piperazine-1-carbonyl]-hexanoic acid hydroxyamide.
6-(4-ethoxy-phenyl)-2S-hydroxy-3R-[4-(toluene-4-sulfonyl)-piperazine-1-carbonyl]-hexanoic acid hydroxyamide.

3R-[4-(5-bromo-thiophene-2-sulfonyl)-piperazine-1-carbonyl]-6-(4-ethoxy-phenyl)-2S-hydroxy-hexanoic acid hydroxyamide.

3R-[4-(5-benzenesulfonyl-thiophene-2-sulfonyl)-piperazine-1-carbonyl]-6-(4-ethoxy-phenyl)-2S-hydroxy-hexanoic acid hydroxyamide.

3R-[4-(4-butoxy-benzenesulfonyl)-piperazine-1-carbonyl]-6-(4-ethoxy-phenyl)-2S-hydroxy-hexanoic acid hydroxyamide.

6-(4-ethoxy-phenyl)-2S-hydroxy-3R-[4-(4-methoxy-2,3,6-trimethyl-benzenesulfonyl)-piperazine-1-carbonyl]-hexanoic acid hydroxyamide.

3R-[4-(3,4-dimethoxy-benzenesulfonyl)-piperazine-1-carbonyl]-6-(4-ethoxy-phenyl)-2S-hydroxy-hexanoic acid hydroxyamide.

6-(4-methoxy-phenyl)-2S-hydroxy-3R-[4-(2-fluoro-phenyl)-piperazine-1-carbonyl]-hexanoic acid hydroxyamide.

6-(4-methoxy-phenyl)-2S-hydroxy-3R-(4-pyridin-2-yl-piperazine-1-carbonyl)-hexanoic acid hydroxyamide.

6-(4-fluoro-phenyl)-3R-[4-(2-fluoro-phenyl)-piperazine-1-carbonyl]-2S-hydroxy-hexanoic acid hydroxyamide.

6-(4-fluoro-phenyl)-2S-hydroxy-3R-(4-pyridin-2-yl-piperazine-1-carbonyl)-hexanoic acid hydroxyamide.

3R-(4-benzyl-2S-methyl-piperazine-1-carbonyl)-6-(4-ethoxy-phenyl)-2S-hydroxy-hexanoic acid hydroxyamide.

3R-(4-benzyl-2S-methyl-piperazine-1-carbonyl)-6-(4-methoxy-phenyl)-2S-hydroxy-hexanoic acid hydroxyamide.

3R-(4-benzyl-2S-1-butyl-piperazine-1-carbonyl)-6-(4-methoxy-phenyl)-2S-hydroxy-hexanoic acid hydroxyamide.

3R-(4-benzyl-2S-methyl-piperazine-1-carbonyl)-6-(4-fluoro-phenyl)-2S-hydroxy-hexanoic acid hydroxyamide.

3R-(4-benzyl-2S-1-butyl-piperazine-1-carbonyl)-6-(4-fluoro-phenyl)-2S-hydroxy-hexanoic acid hydroxyamide.

4-[5-(4-ethoxy-phenyl)-2R-(1S-hydroxy-hydroxycarbamoyl-methyl)-pentanoyl]-2S-methyl-piperazine-1-carboxylic acid tert-butyl ester.

4-[5-(4-ethoxy-phenyl)-2R-(1S-hydroxy-hydroxycarbamoyl-methyl)-pentanoyl]-2S-1-butyl-piperazine-1-carboxylic acid tert-butyl ester.

4-[5-(4-methoxy-phenyl)-2R-(1S-hydroxy-hydroxycarbamoyl-methyl)-pentanoyl]-2S-methyl-piperazine-1-carboxylic acid tert-butyl ester.

4-[5-(4-methoxy-phenyl)-2R-(1S-hydroxy-hydroxycarbamoyl-methyl)-pentanoyl]-2S-1-butyl-piperazine-1-carboxylic acid tert-butyl ester.

4-[5-(4-fluoro-phenyl)-2R-(1S-hydroxy-hydroxycarbamoyl-methyl)-pentanoyl]-2S-methyl-piperazine-1-carboxylic acid tert-butyl ester.

4-[5-(4-fluoro-phenyl)-2R-(1S-hydroxy-hydroxycarbamoyl-methyl)-pentanoyl]-2S-1-butyl-piperazine-1-carboxylic acid tert-butyl ester.

6-(4-ethoxy-phenyl)-2S-methoxy-3R-[4-(2-fluoro-phenyl)-piperazine-1-carbonyl]-hexanoic acid hydroxyamide.

As mentioned above, the present compounds are useful in human or veterinary medicine since they are active as inhibitors of MMPs, in particular as selective inhibitors of MMP-12 (and/or MMP-9) relative to MMP-1 and other collagenases and stromelysins. Accordingly in another aspect, this invention concerns:

(i) a method of management (by which is meant treatment or prophylaxis) of diseases or conditions responsive to inhibition of MMP-12 and/or MMP-9 in mammals, in particular in humans, which method comprises administering to the mammal an effective amount of a compound of formula (I) defined above, or a pharmaceutically acceptable salt thereof; and (ii) a compound of formula (I) defined above, for use in human or veterinary medicine, particularly in the management (by which is meant treatment or prophylaxis) of diseases or conditions responsive to inhibition of MMP-12 and/or MMP-9. (Diseases or conditions responsive to inhibition of MMP-12 and/or MMP-9 include bone resorption, tumour growth or invasion by secondary metastases; rheumatoid arthritis, septic arthritis, osteoarthritis, periodontitis, gingivitis, corneal ulceration, cardiac hypertrophy, acute respiratory distress syndrome, neuroinflammatory disorders, e.g. multiple sclerosis; restenosis; emphysemia; fibrotic didease e.g. fibrosis post radiotherapy, kerotid scarring, liver fibrosis and cystic fibrosis; chronic obstructive pulmonary disease; bronchitis; asthma; autoimmune disease; transplant rejection (e.g. graft versus host disease); cystic fibrosis; psoriasis; psoriatic arthritis; degenerative cartilage loss; inflammatory gastric conditions, e.g. Crohn's disease, inflammatory bowel disease, and ulcerative colitis; atopic dermatitis, epidermolysis bullosa; epidermic ulceration; a neuropathy or nephropathy e.g. interstitial nephritis, glomerulonephriris or renal failure; ocular inflammation; liver cirrhosis, Sjoegren's syndrome; or an inflammatory condition of the nervous system.); and (iii) a compound of formula (I) for use as a medicament; and (iv) the use of a compound of formula (I) defined above in the preparation of an agent for the management (by which is meant treatment or prophylaxis) of diseases or conditions responsive to inhibition of MMP-12 and/or MMP-9; and (v) the use of a compound of formula (I) for the preparation of a medicament for the prevention or treatment of a disease selected from inflammatory diseases including multiple sclerosis, emphysemia, bronchitis, asthma, and a disease related to MMP-12 and/or MMP-9.

In a further aspect of the invention there is provided a pharmaceutical or veterinary composition comprising a compound of formula (I) defined above together with a pharmaceutically or veterinarily acceptable excipient or carrier.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy. Optimum dose levels and frequency of dosing will be determined by clinical trial.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

Compounds of formula (I) may be prepared by standard literature methods, as illustrated in the Examples herein. In general, the compounds wherein R is hydrogen may be prepared by coupling a dioxolane-protected di-carboxylic acid of formula (III) with the desired cyclic amine $HNR_1R_2$:

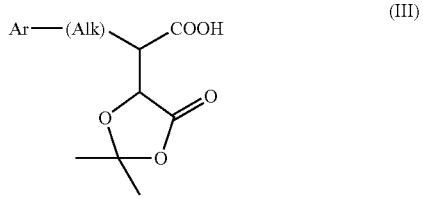
(III)

wherein $R_1$, $R_2$: Ar and Alk are as defined in relation to formula (I), to form the intermediate (IIIA)

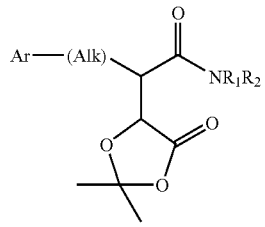
(IIIA)

then reacting intermediate (IIIA) with hydroxylamine.

Methods of coupling amines with carboxylic acids to form amides are very well known, for example from the art of peptide synthesis.

Thus, the invention also includes
(vi) a compound of formula (IIIB) wherein $R_1$, $R_2$, Ar and Alk are as defined in relation to formula (I)
(vii) a process for the preparation of a compound of formula (I) defined above, comprising the deprotection and/or transformation of a compound of formula (IIIA) as defined above,) wherein $R_1$, $R_2$, Ar and Alk are as defined in relation to formula (I)
(viii) a process for the preparation of a compound of formula (IIIA) comprising the step of reacting a compound of formula (III) with a cyclic amine $HNR_1R_2$, wherein $R_1$, $R_2$: Ar and Alk are as defined in relation to formula (I), The following preparative Examples describe the preparation of compounds useful in accordance with the invention The following abbreviations have been used in the examples:
AcOEt—Ethyl acetate
$CH_3CN$—Acetonitrile
DMF—N,N-Dimethylformamide
HOBT—1-Hydroxybenzotriazole
HOAT—1-Hydroxyazobenzotriazole
$MgSO_4$—Magnesium sulfate
Pfp—Pentafluorophenol
WSCDI—N-(3-Dimethylaminopropyl)-N'-ethylcarbodiimide hydrochloride
HCl—Hydrochloric acid
$P(O\text{-}Tol)_3$—Tri-O-tolylphosphine
THF—Tetrahydrofuran
TFA—Trifluoroacetic acid
Z—Benzyloxycarbonyl

EXAMPLE 1

6-(4-ethoxy-phenyl)-2S-hydroxy-3R-(pyrrolidine-1-carbonyl)-hexanoic acid hydroxyamide Scheme 1

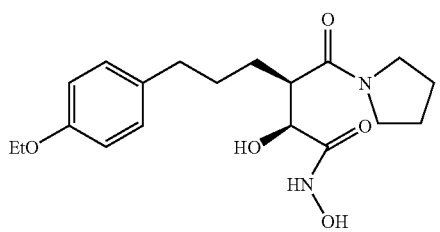

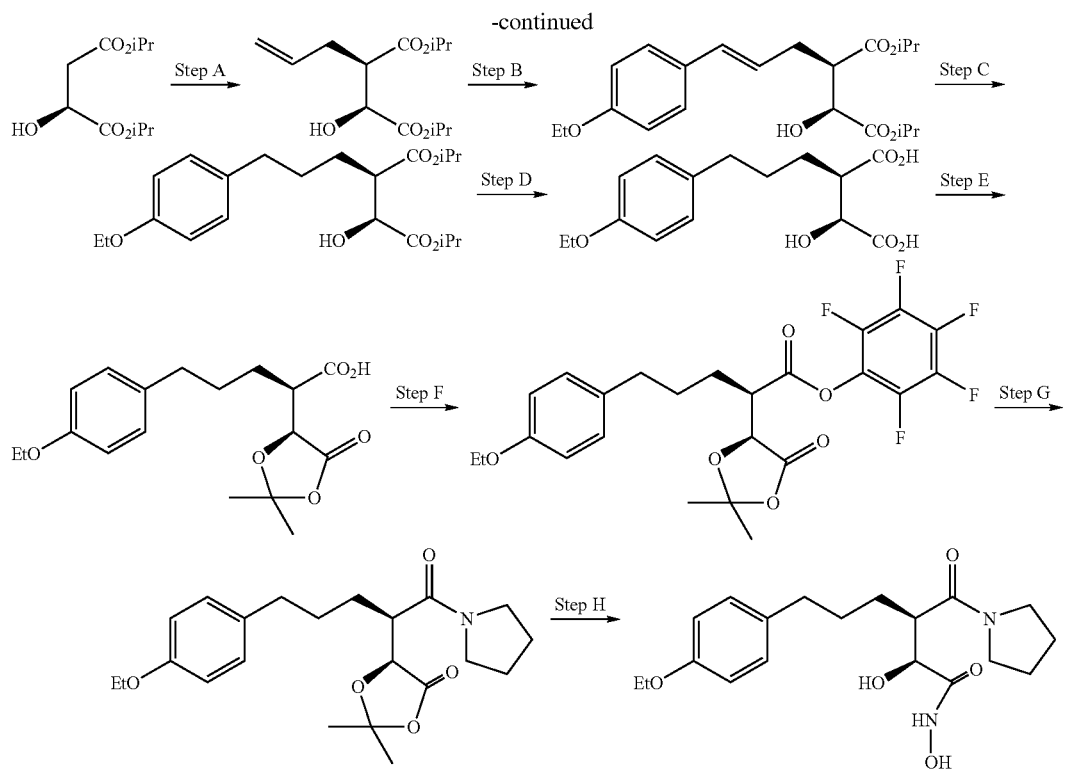

Reagents and conditions. A: LiHMDS, AllBr, THF, -78 C. to RT; B: ArBr, P(o-Tol)₃, Pd(OAc)₂, NET₃, CH₃CN; C: 10% Pd/C, H₂, MeOH; D: LiOH, MeOH, H₂O; E: CuCl₂, dimethoxypropane, acetone; F: pentafluorophenol, WSCDI, HOAt, CH₂Cl₂; G: pyrrolidine, NEt₃, CH₂Cl₂, H: $_{aq}$NH₂OH, iPrOH Example 1 was prepared as outlined in Scheme 1 using procedures described below.

Step A: 2R-allyl-3S-hydroxy-succinic acid diisopropylester.

To a cold (−78 C) solution of 2S-hydroxy-succinic acid diisopropyl ester (19.70 ml, 95 mmol) in THF (35 ml) was added LiHMDS (200 ml, 0.2 mol, 2.1 eq.) dropwise. The reaction mixture was stirred at −78 C for two hours and then at −30 C for 30 min. The reaction mixture was then cooled to −78 C and allyl bromide (12.36 ml, 0.14 mol, 1.5 eq.) added dropwise. The reaction mixture was then allowed to warm to RT overnight. It was poured into a saturated solution of NH₄Cl/ice (200 ml). Extraction with AcOEt (3×200 ml) followed by a wash with water (50 ml) and with brine (50 ml) afforded a yellow oil after removal of the solvents under vacuo. Purification by flash chromatography gave 2R-allyl-3S-hydroxy-succinic acid diisopropylester as a colourless oil (7.76 g, de=80%, 40% yield).

¹H-NMR; delta (CDCl₃): 5.77-5.88 (1H, m), 4.98-5.21 (4H, m), 4.22 (1H, brs), 3.18 (1H, brs), 2.87-2.94 (1H, m), 2.56-2.65 (1H, m), 2.40-2.48 (1H, m), 1.29 (6H, d, J=6.3 Hz), 1.22 (6H, d, J=6.3 Hz).

LRMS: +ve ion 281 (M+Na).

Step B: 2R-[3-(4-ethoxy-phenyl)-allyl]-3S-hydroxy-succinic acid diisopropyl ester.

To a solution of 2R-allyl-3S-hydroxy-succinic acid diisopropylester (4.79 g, 18.5 mmol), 4-bromo phenetole (3.19 ml, 22.2 mmol, 1.2 eq.) and NEt₃ (6.22 ml, 44.6 mmol, 2.4 eq.) in CH₃CN (40 ml), was added a sonicated (for 2 min) suspension of P(O-Tol)₃ (0.57 g, 2.22 mmol, 0.1 eq.) and Pd(OAc)₂ (209 mg, 5%) in CH₃CN (5 ml). The reaction mixture was heated to reflux for 2 hrs. CH₃CN was removed under vacuo. The crude was extracted with AcOEt (3×200 ml), washed with water (50 ml) and with brine (50 ml). A purification by flash chromatography afforded the desired 2R-[3-(4-ethoxy-phenyl)-allyl]-3S-hydroxy-succinic acid diisopropyl ester (5.92 g, 84% yield).

¹H-NMR; delta (CDCl₃): 7.28 (2H, d, J=8.8 Hz), 6.83 (2H, d, J=8.8), 6.46 (1H, d, J=15.7 Hz), 6.02-6.12 (1H, m), 4.98-5.13 (2H, m), 4.26 (1H, dd, J=7.1, 3.0 Hz), 4.02 (2H, q, J=7.0 Hz): 3.23 (1H, d, J=7.1 Hz), 2.92-2.97 (1H, m), 2.68-2.79 (1H, m), 2.49-2.62 (1H, m), 1.41 (3H, t, J=7.0 Hz), 1.19-1.30 (12H, m).

LRMS: +ve ion 401 (M+Na).

Step C: 2R-[3-(4-ethoxy-phenyl)-propyl]-3S-hydroxy-succinic acid diisopropyl ester.

To a solution of 2R-[3-(4-ethoxy-phenyl)-allyl]-3S-hydroxy-succinic acid diisopropyl ester (129 mg, 0.34 mmol) in MeOH (10 ml) under an inert atmosphere, was added 10% Pd/C (13 mg). H₂ was bubbled through the resulting suspension for 30 min. The reaction mixture was then stirred under 1 atmosphere of H₂ for 16 hrs. Pd/C was filtered off and the solvent removed under reduced pressure to give 2R-[3-(4-ethoxy-phenyl)-propyl]-3S-hydroxy-succinic acid diisopropyl ester (115 mg, 88% yield).

¹H-NMR; delta (CDCl₃): 7.08 (2H, d, J=8.6 Hz), 6.81 (2H, d, J=8.6), 4.97-5.14 (2H, m), 4.20 (1H, dd, J=7.3, 3.5 Hz), 4.01 (2H, q, J=7.0 Hz), 3.18 (1H, d, J=7.3 Hz), 2.77-2.83 (1H, m), 2.55-2.62 (2H, m), 1.45-1.94 (4H, m), 1.40 (3H, t, J=7.0 Hz), 1.12-1.30 (12H, m).

LRMS: +ve ion xx (M+Na).

Step D: 2R-[3-(4-ethoxy-phenyl)-propyl]-3S-hydroxy-succinic acid.

To a solution of 2R-[3-(4-ethoxy-phenyl)-propyl]-3S-hydroxy-succinic acid diisopropyl ester (4.78 g, 12.6 mmol) in THF/water (3:1, 120 ml) was added NaOH (1.66 g, 41.5 mmol, 5.5 eq.). The reaction mixture was then stirred for 16 hrs at RT. The mixture was concentrated under reduced pressure and acidify to pH=3 by addition of HCl 1N. The hydroxy diacid was extracted with AcOEt. The organic layer was dried over MgSO$_4$ and the solvent removed under reduced pressure to give the desired 2R-[3-(4-ethoxy-phenyl)-propyl]-3S-hydroxy-succinic acid (3.66 g, 85% yield).

$^1$H-NMR; delta (MeOD): 7.07 (2H, d, J=8.6 Hz), 6.79 (2H, d, J=8.6), 4.23 (1H, d, J=5.8 Hz), 3.98 (2H, q, J=7.0 Hz), 2.76-2.81 (1H, m), 2.53-2.59 (2H, m), 1.55-1.72 (4H, m), 1.35 (3H, t, J=7.0 Hz).

LRMS: +ve ion 319 (M+Na); –ve ion 295 (M–H).

Step E: 2R-(2,2-dimethyl-5-oxo-[1,3]dioxolan-4S-yl)-5-(4-ethoxy-phenyl)-pentanoic acid.

To a solution of 2R-[3-(4-ethoxy-phenyl)-propyl]-3S-hydroxy-succinic acid (3.66 g, 12.3 mmol) in acetone (50 ml) under an inert atmosphere were added dimethoxy propane (2.58 ml, 21 mmol, 1.7 eq.) and copper chloride (165 mg, 1.2 mmol, 0.1 eq.). The reaction mixture was stirred at RT for 16 hrs. The solvent was then removed under vacuo to give 2R-(2,2-dimethyl-5-oxo-[1,3]dioxolan-4S-yl)-5-(4-ethoxy-phenyl)-pentanoic acid (4.03 g, 97% yield).

$^1$H-NMR; delta (CDCl$_3$): 7.08 (2H, d, J=8.5 Hz), 6.82 (2H, d, J=8.5), 4.48 (1H, d, J=4.8 Hz), 4.01 (2H, q, J=7.0 Hz), 2.91-2.98 (1H, m), 2.54-2.64 (3H, m), 1.23-2.20 (4H, m), 1.58 (3H, s), 1.53 (3H, s), 1.40 (3H, t, J=7.0 Hz).

LRMS: +ve ion 359 (M+Na); –ve ion 335 (M–H).

Step F. 2R-(2,2-dimethyl-5-oxo-[1,3]dioxolan-4S-yl)-5-(4-ethoxy-phenyl)-pentanoic acid pentafluorophenyl ester.

To a cold (0 C) solution of 2R-(2,2-dimethyl-5-oxo-[1,3]dioxolan-4S-yl)-5-(4-ethoxy-phenyl)-pentanoic acid (4.03 g, 12 mmol) and pentafluoro phenol (2.43 g, 13.2 mmol, 1.1 eq.) in CH$_2$Cl$_2$ (50 ml) was added WSC (2.54 g, 13.2 mmol, 1.1 eq.). The reaction mixture was allowed to warm to RT overnight. CH$_2$Cl$_2$ was removed under vacuo and the resulting crude reaction mixture was dissolved in AcOEt (200 ml). The organic layer was washed with water (50 ml), NaHCO$_3$ sat (20 ml) and finally with brine (20 ml). Solvent was removed under reduced pressure to give an oil which was purified by flash chromatography to furnish the expected 2R-(2,2-dimethyl-5-oxo-[1,3]dioxolan-4S-yl)-5-(4-ethoxy-phenyl)-pentanoic acid pentafluorophenyl ester (3.94 g, 65% yield).

$^1$H-NMR; delta (CDCl$_3$): 7.09 (2H, d, J=8.4 Hz), 6.83 (2H, d, J=8.4 Hz), 4.56 (1H, d, J=6.0 Hz), 4.01 (2H, q, J=7.0 Hz), 3.20-3.28 (1H, m), 2.64 (2H, t, J=7.6 Hz), 1.98-2.08 (2H, m), 1.70-1.86 (2H, m), 1.62 (3H, s), 1.57 (3H, s), 1.40 (3H, t, J=7.0 Hz).

Step G. 5-(4-Ethoxy-phenyl)-2R-[(2,2-dimethyl-5-oxo-[1,3]dioxolan-4S-yl)]-1-pyrrolidin-1-yl-pentan-1-one.

To a solution of 2R-(2,2-dimethyl-5-oxo-[1,3]dioxolan-4S-yl)-5-(4-ethoxy-phenyl)-pentanoic acid pentafluorophenyl ester (150 mg, 0.30 mmol) in CH$_2$Cl$_2$ (10 ml) was added pyrrolidine (30 µl, 0.36 mmol, 1.2 eq.). The reaction mixture was stirred for 16 hrs and the solvent was removed under vacuo. The crude was taken-up in AcOEt (70 ml) and washed with water (10 ml), then with NaHCO$_3$ sat (10 ml) and finally with brine (10 ml). The solvent was dried over MgSO$_4$ and removed under reduced pressure to give the desired 5-(4-Ethoxy-phenyl)-2R-[(2,2-dimethyl-5-oxo-[1,3]dioxolan-4S-yl)]-1-pyrrolidin-1-yl-pentan-1-one (116 mg, quant.).

$^1$H-NMR; delta (CDCl$_3$): 7.05 (2H, d, J=8.6 Hz), 6.8 (2H, d, J=8.6 Hz), 4.55 (1H, d, J=8.4 Hz), 3.99 (2H, m), 3.8-3.3 (10H, m), 3.05 (1H, m), 2.55 (2H, t, J=7.6 Hz), 2.1-1.7 (2H, m), 1.6 (3H, s), 1.5 (3H, s), 1.4 (3H, t, J=7.0 Hz).

LRMS: +ve ion 405 (M+H), 428 (M+Na).

Step H. 6-(4-ethoxy-phenyl)-2S-hydroxy-3R-(pyrrolidine-1-carbonyl)-hexanoic acid hydroxyamide.

To a solution of 5-(4-Ethoxy-phenyl)-2R-[(2,2-dimethyl-5-oxo-[1,3]dioxolan-4S-yl)]-1-pyrrolidin-1-yl-pentan-1-one (116 mg, 0.30 mmol) in i-PrOH (5 ml), was added an aqueous solution of hydroxylamine (50%, 99 µl, 1.5 mmol, 5 eq.). The reaction mixture was allowed to stir at RT for 16 hrs. The solvent was removed under reduced pressure to yield an oil which was purified by preparative reverse phase chromatography to give the required product.

$^1$H-NMR; delta (CD$_3$OD): 7.05 (2H, d, J=8.6 Hz), 6.8 (2H, d, J=8.6 Hz), 4.0 (4H, m), 3.85 (1H, m), 3.7 (1H, m), 3.4 (2H, m), 3.1 (1H, m), 2.55 (2H, m), 1.9-1.5 (7H, m), 1.35 (3H, t, J=7.0 Hz).

LRMS: +ve ion 387 (M+Na); –ve ion 363 (M–H)

The compounds of Examples 2-20 were prepared by the method of Example 1 by parallel synthesis, using the appropriate amine in Step G. The products were purified by preparative HPLC.

EXAMPLE 2

3R-(6,7-dimethoxy-3,4-dihydro-1H-isoquinoline-2-carbonyl)-6-(4-ethoxy-phenyl)-2S-hydroxy-hexanoic acid hydroxyamide

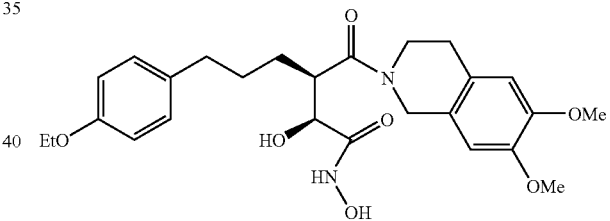

LRMS: +ve ion 487 (M+H), 509 (M+Na); –ve ion 485 (M–H).

EXAMPLE 3

6-(4-ethoxy-phenyl)-2S-hydroxy-3R-[4-(3-methoxy-phenyl)-piperazine-1-carbonyl]-hexanoic acid hydroxyamide

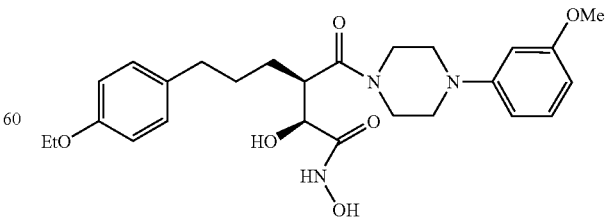

LRMS: +ve ion 486 (M+H), 508 (M+Na); –ve ion 484 (M–H).

EXAMPLE 4

6-(4-ethoxy-phenyl)-2S-hydroxy-3R-[4-(4-methoxy-phenyl)-piperazine-1-carbonyl]-hexanoic acid hydroxyamide

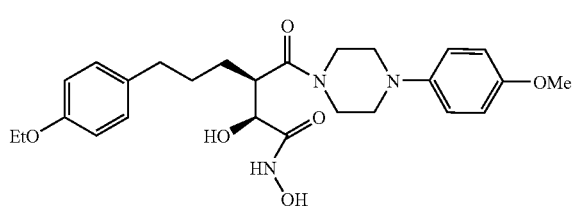

LRMS: +ve ion 486 (M+H), 508 (M+Na); +ve ion 484 (M−H).

EXAMPLE 5

6-(4-ethoxy-phenyl)-2S-hydroxy-3R-(4-pyridin-2-yl-piperazine-1-carbonyl)-hexanoic acid hydroxyamide

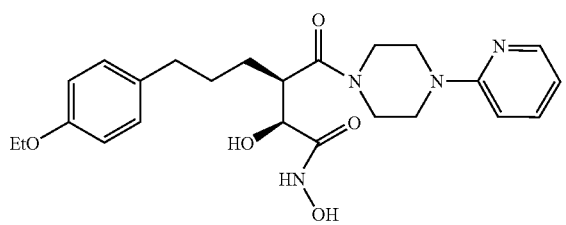

$^1$H-NMR; delta (CD$_3$OD): 8.1 (1H, d, J=1.4 Hz), 7.55 (1H, m), 7.05 (2H, d, J=8.7 Hz), 6.9-6.6 (4H, m), 3.95 (1H, d, J=7.0 Hz), 3.55 (4H, m), 2.55 (1H, m), 1.8-1.5 (6H, m), 1.35 (3H, m).
LRMS: +ve ion 457 (M+H); −ve ion 455 (M−H).

EXAMPLE 6

6-(4-ethoxy-phenyl)-2S-hydroxy-3R-(4-pyridin-4-yl-piperazine-1-carbonyl)-hexanoic acid hydroxyamide

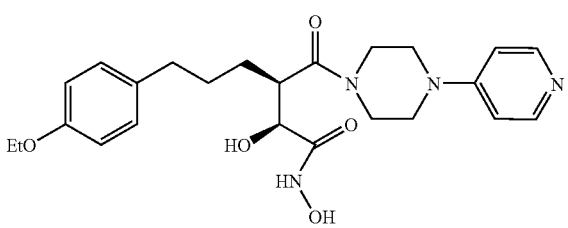

EXAMPLE 7

6-(4-ethoxy-phenyl)-2S-hydroxy-3R-(morpholine-4-carbonyl)-hexanoic acid hydroxyamide

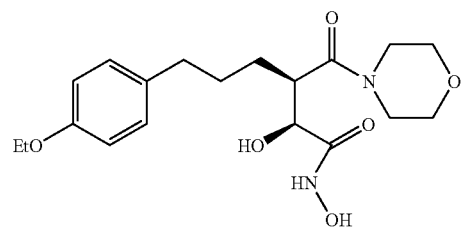

$^1$H-NMR; delta (CD$_3$OD): 7.05 (2H, d, J=8.6 Hz), 6.8 (2H, d, J=8.6 Hz), 4.05-3.90 (3H, m), 3.8-3.4 (8H, m), 2.55 (2H, t, J=6.7 Hz), 1.75-1.4 (4H, m), 1.35 (3H, t, J=7.0 Hz).
LRMS: +ve ion 403 (M+Na); −ve ion 379 (M−H).

EXAMPLE 8

6-(4-ethoxy-phenyl)-2S-hydroxy-3R-(2RS-methyl-morpholine-4-carbonyl)-hexanoic acid hydroxyamide

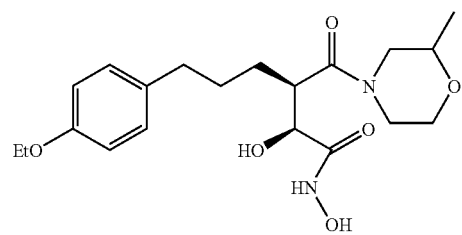

LRMS: +ve ion 417 (M+Na), 395 (M+H); −ve ion 393 (M−H).

EXAMPLE 9

6-(4-ethoxy-phenyl)-2S-hydroxy-3R-(2,6-RS-dimethyl-morpholine-4-carbonyl)-hexanoic acid hydroxyamide

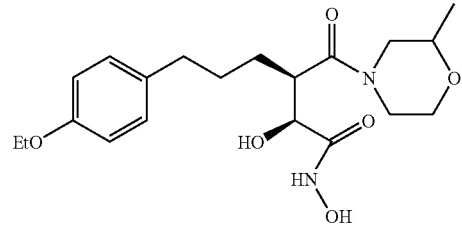

LRMS: +ve ion 431 (M+Na), 409 (M+H); −ve ion 407 (M−H).

EXAMPLE 10

6-(4-ethoxy-phenyl)-2S-hydroxy-3R-(thiomorpholine-4-carbonyl)-hexanoic acid hydroxyamide

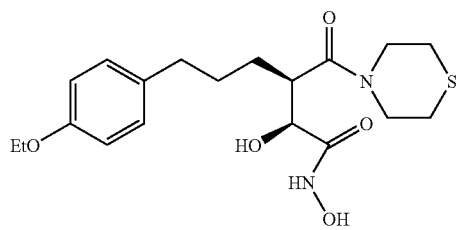

$^1$H-NMR; delta (CD$_3$OD): 7.05 (2H, d), 6.8 (2H, d), 4.0 (5H, m), 3.8-3.5 (2H, m), 2.9-2.4 (7H, m), 1.55 (4H, m) and 1.3 (3H, t).
LRMS: +ve ion 419 (M+Na). 397 (M+H); −ve ion 395 (M−H).

EXAMPLE 11

3R-(4-benzyl-piperidine-1-carbonyl)-6-(4-ethoxy-phenyl)-2S-hydroxy-hexanoic acid hydroxyamide

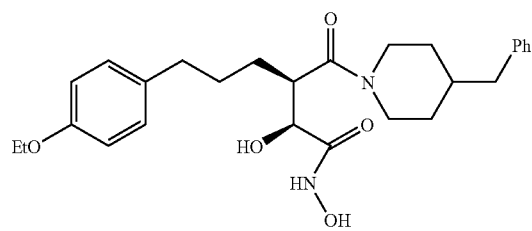

$^1$H-NMR; delta (CD$_3$OD): 7.3-7.0 (8H, m), 6.8 (2H, m), 4.55 (1H, d, J=12.4 Hz), 4.05 (2H, dd, J=2.0 Hz), 3.9 (2H, m), 2.9 (1H, m), 2.6-2.4 (5H, m), 1.84 (1H, d, J=2.9 Hz), 1.7-1.5 (6H, m), 1.35 (3H, t, J=7.0 Hz).
LRMS: +ve ion 491 (M+Na); −ve ion 467 (M−H).

EXAMPLE 12

3R-(4-benzo[1,3]dioxol-5-ylmethyl-piperazine-1-carbonyl)-6-(4-ethoxy-phenyl)-2S-hydroxy-hexanoic acid hydroxyamide

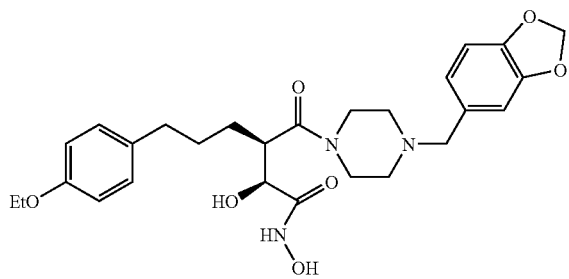

LRMS: +ve ion 514 (M+H); −ve ion 512 (M−H).

EXAMPLE 13

6-(4-ethoxy-phenyl)-2S-hydroxy-3R-(4-pyridin-4-ylmethyl-piperazine-1-carbonyl)-hexanoic acid hydroxyamide

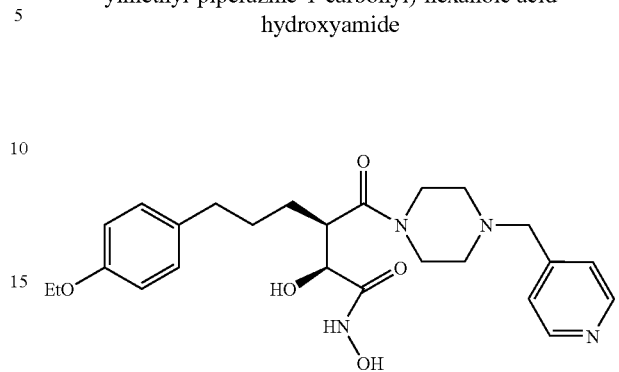

LRMS: +ve ion 471 (M+H); −ve ion 469 (M−H).

EXAMPLE 14

6-(4-ethoxy-phenyl)-2S-hydroxy-3R-(4-benzylpiperazine-1-carbonyl)-hexanoic acid hydroxyamide

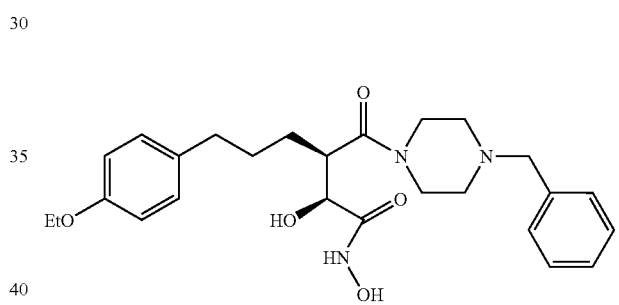

LRMS: +ve ion 471 (M+H); −ve ion 469 (M−H).

EXAMPLE 15

6-(4-ethoxy-phenyl)-2S-hydroxy-3R-(4-pyrimidin-2-yl-piperazine-1-carbonyl)-hexanoic acid hydroxyamide

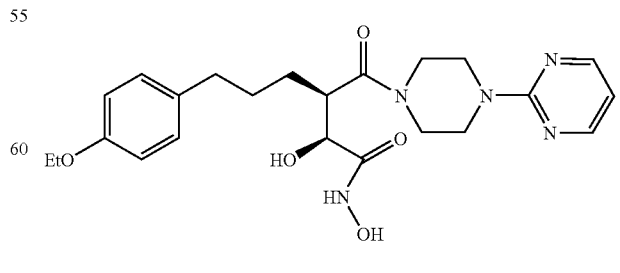

LRMS: +ve ion 458 (M+H); −ve ion 456 (M−H).

EXAMPLE 16

6-(4-ethoxy-phenyl)-2S-hydroxy-3R-[4-(4-trifluoromethyl-pyrimidin-2-yl)-piperazine-1-carbonyl]-hexanoic acid hydroxyamide

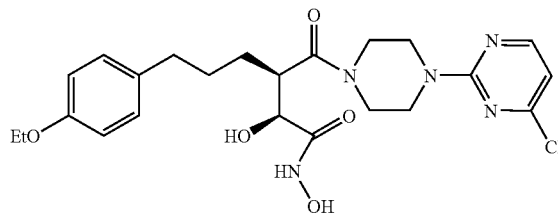

LRMS: +ve ion 526 (M+H), 548 (M+Na); −ve ion 524 (M−H).

EXAMPLE 17

6-(4-ethoxy-phenyl)-2S-hydroxy-3R-[4-(4-chloro-pyrimidin-2-yl)-piperazine-1-carbonyl]-hexanoic acid hydroxyamide

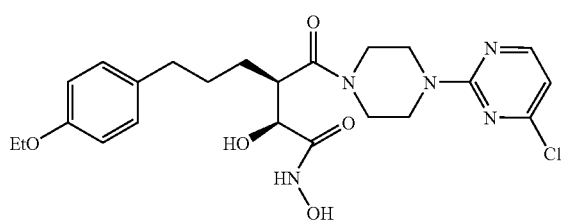

LRMS: +ve ion 492 (M+H); −ve ion 490 (M−H).

EXAMPLE 18

3R-[4-(4,6-dimethoxy-[1,3,5]triazin-2-yl)-piperazine-1-carbonyl]-6-(4-ethoxy-phenyl)-2S-hydroxy-hexanoic acid hydroxyamide

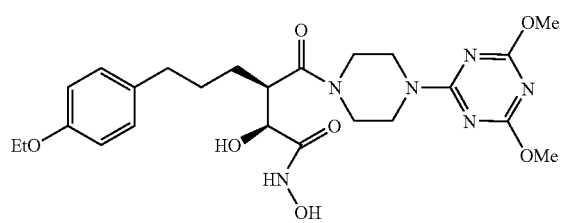

LRMS: +ve ion 519 (M+H); −ve ion 517 (M−H).

EXAMPLE 19

6-(4-ethoxy-phenyl)-2S-hydroxy-3R-[4-(3-trifluoromethyl-phenyl)-piperazine-1-carbonyl]-hexanoic acid hydroxyamide

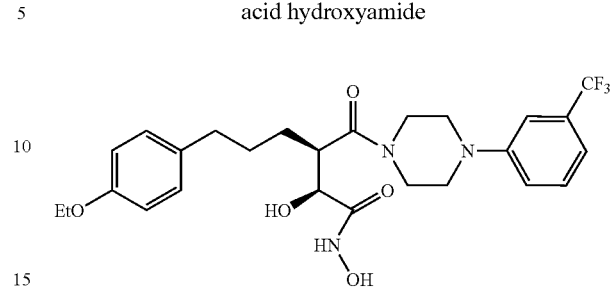

LRMS: +ve ion 524 (M+H); −ve ion 522 (M−H).

EXAMPLE 20

6-(4-ethoxy-phenyl)-2S-hydroxy-3R-[4-(2-fluoro-phenyl)-piperazine-1-carbonyl]-hexanoic acid hydroxyamide

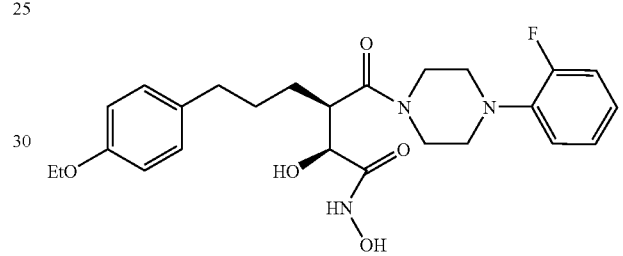

LRMS: +ve ion 474 (M+H); −ve ion 472 (M−H).

EXAMPLE 21

3R-[4-(acetyl-methyl-amino)-piperidine-1-carbonyl]-6-(4-ethoxy-phenyl)-2S-hydroxy-hexanoic acid hydroxyamide The compound of Example 21 was prepared as outlined in scheme 2, using procedures described below.

Scheme 2

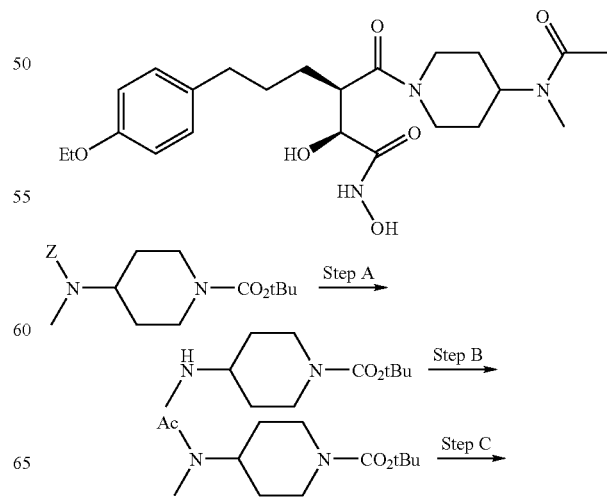

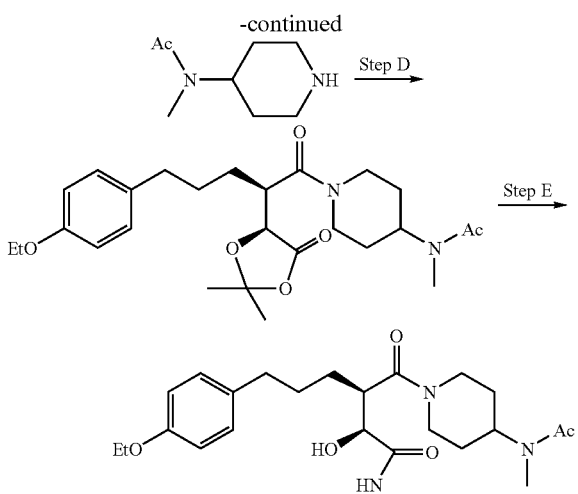

Reagents and conditions: A: H₂, Pd/C, MeOH; B: AcCl, NEt₃, CH₂Cl₂; C: TFA/CH₂Cl₂; D: PFP ester, NEt₃; E: NH₂OH, iPrOH Step A: 4-methylamino-piperidine-1-carboxylic acid tert-butyl ester.

To a solution of 4-(benzyloxycarbonyl-methyl-amino)-piperidine-1-carboxylic acid tert-butyl ester (5 g, 0.014 mmol) in MeOH (30 ml) was added under an inert atmosphere 10% Pd/C (500 mg). H₂ was bubbled through the resulting suspension for 2 hrs. The reaction mixture was then stirred under 1 atm. of H₂ for 2 hrs. Pd/C was filtered off and the solvent was removed under reduced pressure to give the expected 4-methylamino-piperidine-1-carboxylic acid tert-butyl ester (3.08 g, quant.).

Step B: 4-(acetyl-methyl-amino)-piperidine-1-carboxylic acid tert-butyl ester.

To a solution of 4-methylamino-piperidine-1-carboxylic acid tert-butyl ester (616 mg, 2.9 mmol) in CH₂Cl₂ (25 ml), was added acetyl chloride (215 μl, 3.02 mmol, 1.05 eq.) dropwise. The reaction mixture was stirred at RT for 16 hrs. The crude reaction mixture was extracted with CH₂Cl₂ (2×50 ml) and washed with water (10 ml) and with brine (10 ml). The solvent was removed under reduced pressure to give the expected 4-(Acetyl-methyl-amino)-piperidine-1-carboxylic acid tert-butyl ester (708 mg, 96% yield).

¹H-NMR; delta (CDCl₃): 4.7-4.5 (1H, m), 4.1 (2H, br d, J=12.7 Hz), 2.8 (5H, m), 2.1 (5H, m), 1.6 (2H, m), 1.5 (9H, s).

LRMS: +ve ion 215 (M+H).

Step C: N-methyl-N-piperidin-4-yl-acetamide.

To a solution of 4-(acetyl-methyl-amino)-piperidine-1-carboxylic acid tert-butyl ester (525 mg, 2.05 mmol) in AcOEt (5 ml) was added HCl 3N (4 ml). The reaction mixture was stirred at RT for 16 hrs. Solvent were removed under reduced pressure to gine the expected N-methyl-N-piperidin-4-yl-acetamide as its hydrochloride salt (395 mg, quant.).

¹H-NMR; delta (CD₃OD): 4.6 (1H, m), 3.5 (2H, br d, J=12.8 Hz), 3.2-3.1 (2H, m), 3.0-2.85 (3H, m), 2.2 (3H, s), 2.1-1.8 (4H, m).

LRMS: +ve ion 157 (M+H).

Step D: N-{1-[2R-(2,2-dimethyl-5-oxo-[1,3]dioxolan-4S-yl)-5-(4-ethoxy-phenyl)-pentanoyl]-piperidin-4-yl}-N-methyl-acetamide.

To a solution of 2R-(2,2-dimethyl-5-oxo-[1,3]dioxolan-4S-yl)-5-(4-ethoxy-phenyl)-pentanoic acid pentafluorophenyl ester (230 mg, 0.46 mmol) in CH₂Cl₂ (5 ml) was added N-Methyl-N-piperidin-4-yl-acetamide (137 mg, 0.6 mmol, 1.3 eq.) followed by NEt₃(257 μl, 1.83 mmol, 4 eq.). The reaction mixture was stirred at RT for 16 hrs. The reaction mixture was extracted with CH₂Cl₂ (2×20 ml) and washed with water (10 ml), NaHCO₃ sat (5 ml) and finally with brine (10 ml). The organic layer was dried over MgSO₄ and the solvent were removed under reduced pressure to give the expected N-{1-[2R-(2,2-dimethyl-5-oxo-[1,3]dioxolan-4S-yl)-5-(4-ethoxy-phenyl)-pentanoyl]-piperidin-4-yl}-N-methyl-acetamide in quantitative yield. This compound was used in the next step without any further purification.

¹H-NMR; delta (CDCl₃): 7.05 (2H, d, J=7.2 Hz), 6.7 (2H, d, J=7.2 Hz), 4.75 (2H, m), 4.55 (1H, d, J=7.9 Hz), 4.0 (3H, m), 3.05 (1H, m), 2.8 (1H, m), 2.7-2.5 (4H, m), 2.1 (3H, s), 1.85 (3H, m), 1.75-1.5 (4H, m), 1.65 (3H, s), 1.55 (3H, s), 1.4 (3H, t, J=7.0 Hz), 0.8 (3H, t, J=7.2 Hz).

LRMS: +ve ion 475 (M+H).

Step E: 3R-[4-(acetyl-methyl-amino)-piperidine-1-carbonyl]-6-(4-ethoxy-phenyl)-2S-hydroxy-hexanoic acid hydroxyamide.

To a solution of N-{1-[2R-(2,2-dimethyl-5-oxo-[1,3]dioxolan-4S-yl)-5-(4-ethoxy-phenyl)-pentanoyl]-piperidin-4-yl}-N-methyl-acetamide (135 mg, 0.28 mmol) in i-PrOH (5 ml) was added an aqueous solution of hydroxylamine (50%, 94 μl, 1.43 mmol, 5 eq.). The reaction mixture was allowed to stir at RT for 16 hrs. The solvent was removed under reduced pressure to yield an oil which was purified by preparative reverse phase chromatography to give the required 3R-[4-(acetyl-methyl-amino)-piperidine-1-carbonyl]-6-(4-ethoxy-phenyl)-2S-hydroxy-hexanoic acid hydroxyamide.

LRMS: +ve ion (M+Na); –ve ion (M–H)

EXAMPLE 22

6-(4-ethoxy-phenyl)-2S-hydroxy-3R-[4-(methyl-propyl-amino)-piperidine-1-carbonyl]-hexanoic acid hydroxyamide

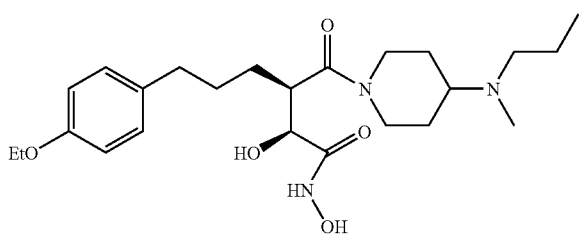

Example 22 was prepared as outlined in Scheme 3 using procedures described below.

Scheme 3

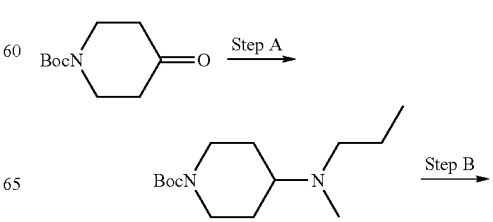

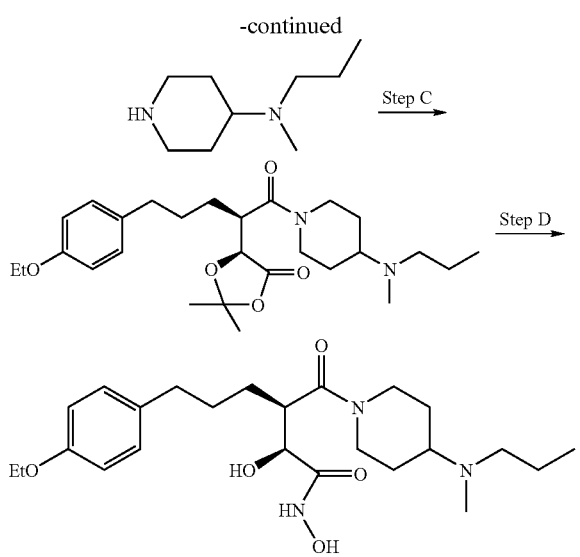

Reagents and conditions: A: methyl propyl amine, ; B: TFA/CH$_2$Cl$_2$; C: PFP ester, NEt$_3$; D: NH$_2$OH, iPrOH Step A: 4-(methyl-propyl-amino)-piperidine-1-carboxylic acid tert-butyl ester.

To a solution of 4-oxo-piperidine-1-carboxylic acid tert-butyl ester (100 mg, 0.5 mmol) in MeOH (5 ml) was added NaBH$_3$CN (32 mg, 0.5 mmol, 1 eq.). The pH of the reaction mixture was adjusted to 5.5 by addition of 5N HCl and stirred for 48 hrs at RT under an inert atmosphere. The solvent was removed under reduced pressure and the crude was taken-up in AcOEt (150 ml). The organic layer was washed with NaHCO$_3$ (10 ml) and with brine (10 ml) and was dried over MgSO$_4$. The solvent was removed under vacuo to give the expected 4-(methyl-propyl-amino)-piperidine-1-carboxylic acid tert-butyl ester (106 mg, 82% yield).

$^1$H-NMR; delta (CDCl$_3$): 4.14 (1H, br d, J=12.2 Hz), 3.8 (1H, m), 3.0 (1H, m), 2.8-2.35 (5H, m), 2.2 (3H, s), 1.9-1.7 (3H, m), 1.5 (11H, s), 0.9 (3H, t, J=3.4 Hz).

LRMS: +ve ion 257 (M+H).

Step B: methyl-piperidin-4-yl-propyl-amine.

To a solution of 4-(methyl-propyl-amino)-piperidine-1-carboxylic acid tert-butyl ester (106 mg, 0.41 mmol) in AcOEt (10 ml) was added 3N HCl (4 ml). The reaction mixture was stirred for 16 hrs at RT. The solvent was removed under reduced pressure to give the desired methyl-piperidin-4-yl-propyl-amine (87 mg, 92% yield).

$^1$H-NMR; delta (CD$_3$OD): 3.95 (1H, m), 3.6 (2H, d, J=13.9 Hz), 2.3 (2H, d, J=11.3 Hz), 2.05 (4H, m), 1.85 (4H, m), 1.05 (3H, t, J=7.3 Hz).

LRMS: +ve ion 157 (M+H).

Step C: 5S-{4-(4-Ethoxy-phenyl)-1R-[4-(methyl-propyl-amino)-piperidine-1-carbonyl]-butyl}-2,2-dimethyl-[1,3]dioxolan-4-one.

To a solution of 2R-(2,2-dimethyl-5-oxo-[1,3]dioxolan-4S-yl)-5-(4-ethoxy-phenyl)-pentanoic acid pentafluorophenyl ester (175 mg, 0.35 mmol) in CH$_2$Cl$_2$ (5 ml) was added methyl-piperidin-4-yl-propyl-amine (87 mg, 0.45 mmol, 1.3 eq.) followed by NEt$_3$ (197 µl, 1.39 mmol, 4 eq.). The reaction mixture was stirred for 16 hrs and the solvent was removed under vacuo. The crude was taken-up in AcOEt (70 ml) and washed with water (10 ml), then with NaHCO$_3$ sat (10 ml) and finally with brine (10 ml). The organic layer was dried over MgSO$_4$ and removed under reduced pressure. A purification on silica gel gave the desired 5S-{4-(4-Ethoxy-phenyl)-1R-[4-(methyl-propyl-amino)-piperidine-1-carbonyl]-butyl}-2,2-dimethyl-[1,3]dioxolan-4-one. (82 mg, 50% yield).

$^1$H-NMR; delta (CDCl$_3$): 7.0 (2H, d, J=8.3 Hz), 6.7 (2H, d, J=8.3 Hz), 4.65 (1H, m), 4.5 (1H, m), 3.9 (2H, m), 3.05 (1H, m), 2.9 (1H, m), 2.5 (4H, d, J=7.7 Hz), 2.3 (2H, m), 2.15 (3H, dd, J=4.0, 13.8 Hz), 1.7 (4H, t, J=7.0 Hz), 1.55 (3H, s), 1.5 (3H, s), 1.45-1.3 (7H, m). 1.3 (3H, t, J=7.0 Hz), 0.8 (3H, t, J=7.2 Hz).

LRMS: +ve ion 475 (M+H).

Step D: 6-(4-ethoxy-phenyl)-2S-hydroxy-3R-[4-(methyl-propyl-amino)-piperidine-1-carbonyl]-hexanoic acid hydroxyamide.

To a solution of 5S-{4-(4-ethoxy-phenyl)-1R-[4-(methyl-propyl-amino)-piperidine-1-carbonyl]-butyl}-2,2-dimethyl-[1,3]dioxolan-4-one (82 mg, 0.17 mmol) in i-PrOH (3 ml), was added an aqueous solution of hydroxylamine (50%, 57 µl, 0.87 mmol, 5 eq.). The reaction mixture was allowed to stir at RT for 16 hrs. The solvent was removed under reduced pressure to yield an oil which was purified by preparative reverse phase chromatography to give the required product.

$^1$H-NMR; delta (CH3OD): 7.1 (2H, d), 6.8 (2H, d), 4.6 (1H, d), 4.1 (1H, d), 4.0 (2H, m), 3.35 (1H, m), 2.9-2.35 (8H, m), 2.3-2.2 (3H, s), 2.0-1.4 (10H, m), 1.35 (3H, t) and 0.9 (3H, t).

LRMS: +ve ion 450 (M+H); −ve ion 448 (M−H)

EXAMPLE 23

6-(4-ethoxy-phenyl)-2S-hydroxy-3R-(3S-benzyl-morpholine-4-carbonyl)-hexanoic acid hydroxyamide

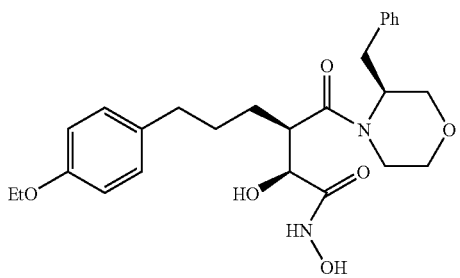

The compound of example 23-25 were prepared by the method of example 1 according to scheme 1, and using the appropriate amine (synthesised according to the procedures described in Tetrahedron, 36, 409-415, 1980 and Journal of Organic Chemistry, 61, 4990-4998, 1996), in Step A. The products were purified by preparative HPLC.

LRMS: +ve ion 471 (M+H); −ve ion 469 (M−H)

EXAMPLE 24

6-(4-ethoxy-phenyl)-2S-hydroxy-3R-(3S-isobutyl-morpholine-4-carbonyl)-hexanoic acid hydroxyamide

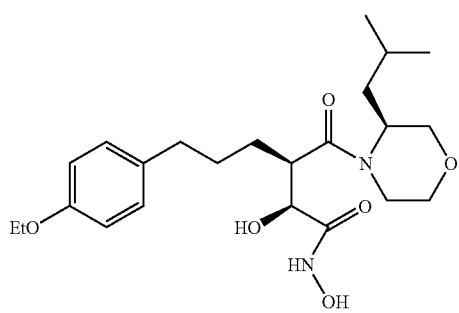

LRMS: +ve ion 437 (M+H); −ve ion 435 (M−H)

EXAMPLE 25

6-(4-ethoxy-phenyl)-2S-hydroxy-3R-(3S-phenyl-morpholine-4-carbonyl)-hexanoic acid hydroxyamide

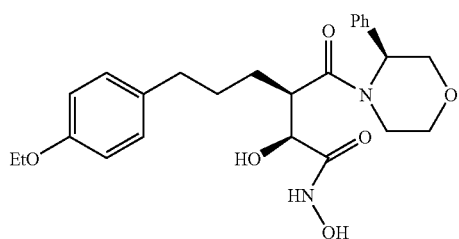

LRMS: +ve ion 457 (M+H), 479 (M+Na); −ve ion 455 (M−H)

EXAMPLE 26

3R-(4-benzyl-3RS-methyl-piperazine-1-carbonyl)-6-(4-ethoxy-phenyl)-2S-hydroxy-hexanoic acid hydroxyamide

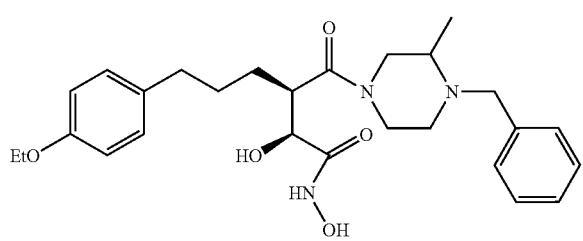

The compound of example 26-28 were prepared by the method of example 1 according to scheme 1, and using the appropriate piperazines (synthesised according to the procedure described in Tetrahedron: *Asymmetry,* 12, 3319-3324, 2001; and Org. Prep. Proced. Int., 22, (6), 761-768, 1990, in Step A. The products were purified by preparative HPLC.

LRMS: +ve ion 484 (M+H).

EXAMPLE 27

3R-(3S,4-dibenzyl-piperazine-1-carbonyl)-6-(4-ethoxy-phenyl)-2S-hydroxy-hexanoic acid hydroxyamide

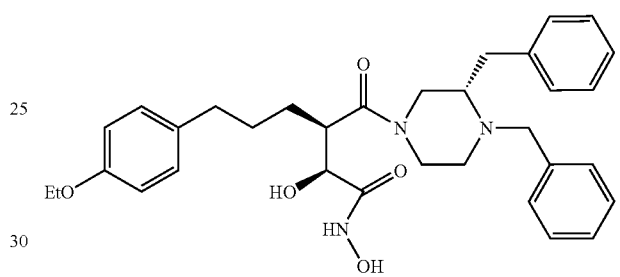

LRMS: +ve ion 560 (M+H).

EXAMPLE 28

3R-(4-benzyl-3RS-phenyl-piperazine-1-carbonyl)-6-(4-ethoxy-phenyl)-2S-hydroxy-hexanoic acid hydroxyamide

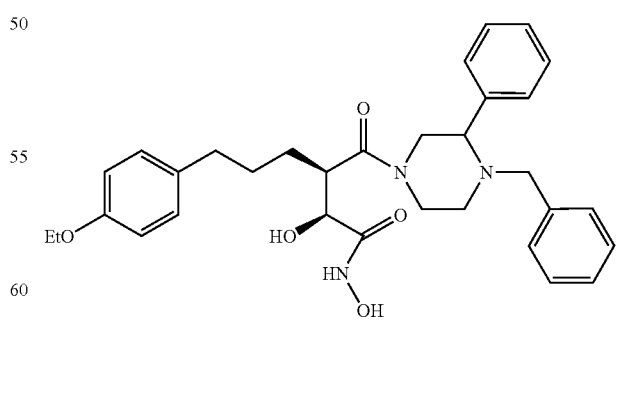

LRMS: +ve ion 546 (M+H).

EXAMPLE 29

4-(4-benzo[1,3]dioxol-5-ylmethyl-piperazin-1-yl)-2S,N-dihydroxy-4-oxo-3R-(4-trifluoromethoxy-benzyl)-butyramide Example 29 was prepared as outlined in Scheme 4 using procedures described below.

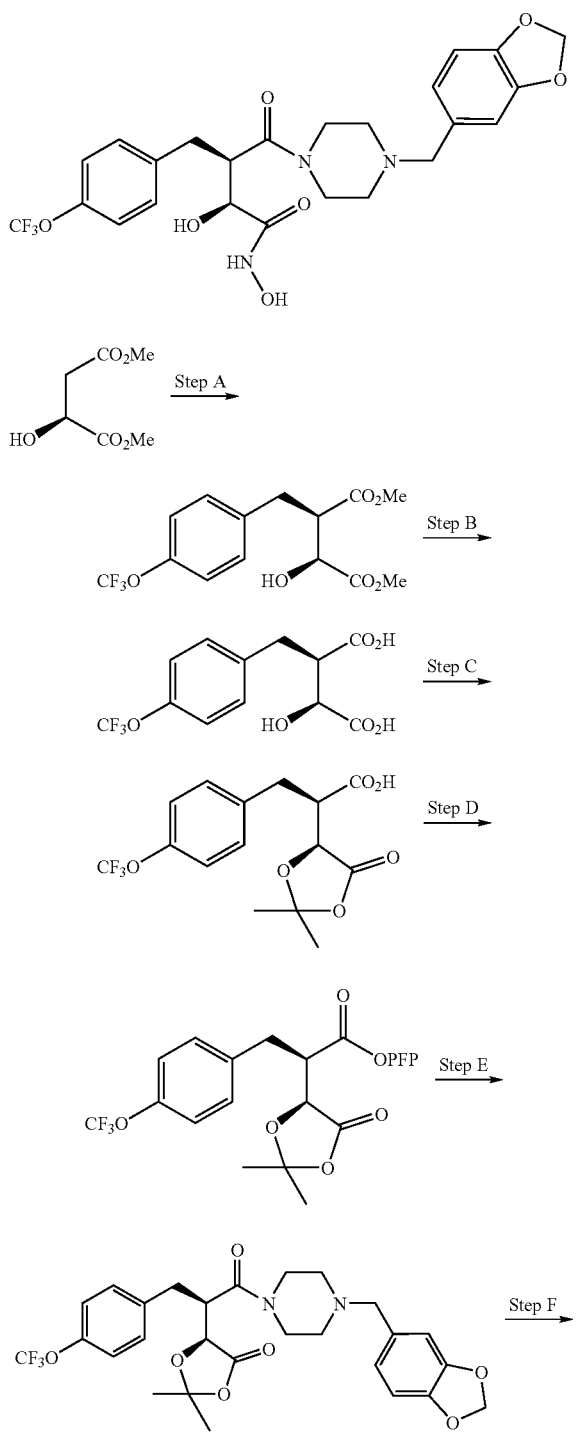

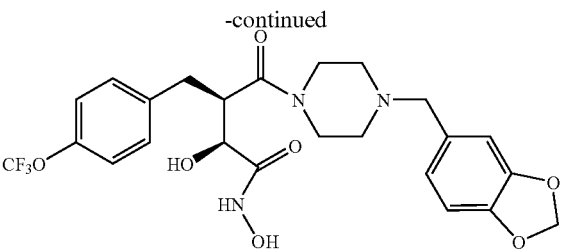

Reagents and conditions. A: LiHMDS, 4-OCF$_3$—C$_6$H$_4$—CH$_2$Br,THF, −78 to RT; B: NaOH, THF, H$_2$O; C: CuCl$_2$, dimethoxyacetone, acetone; D: pentafluorophenol, WSC, HOAt, CH$_2$Cl$_2$; E: RNH$_2$, NEt$_3$CH$_2$Cl$_2$; F: HONH$_2$ $_{aq.}$, iPrOH Step A: 2S-hydroxy-3R-(4-trifluoromethoxy-benzyl)-succinic acid dimethyl ester.

To a cold (−78 C) solution of 2S-hydroxy-succinic acid dimethyl ester (3.0 g, 18.5 mmol) in THF (100 ml), was added a 1N solution of LiHMDS (40.7 ml, 40.7 mmol, 2.2 eq.) dropwise. The reaction mixture was stirred at −78 C for 30 min and then at −30 C for 1 hr. The temperature was brought down to −78 C and 1-bromomethyl-4-trifluoromethoxy-benzene (3.11 ml, 19.4 mmol, 1.05 eq.) was added dropwise. The reaction mixture was allowed to warm to RT overnight and was then poured into NH$_4$Cl$_{sat}$ (50 ml). THF was removed under vacuo and the crude was taken-up in AcOEt (150 ml). The organic layer was washed with water (2×20 ml) and with brine (20 ml) before being dried over MgSO$_4$. Solvent was removed under reduced pressure to give an oil which was purified by flash chromatography on silica gel. The expected 2S-hydroxy-3R-(4-trifluoromethoxy-benzyl)-succinic acid dimethyl ester was obtained in 24% yield (1.50 g).

$^1$H-NMR; delta (CDCl$_3$): 7.31 (2H, d, J=8.5 Hz), 7.15 (2H, d, J=8.4 Hz), 4.12 (1H, d, J=6.5 Hz), 3.75 (3H, s), 3.69 (3H, s), 3.20 (2H, m), 3.01 (1H, m).

LRMS: +ve ion 358 (M+Na).

Step B: 2S-hydroxy-3R-(4-trifluoromethoxy-benzyl)-succinic acid.

To a cold (0 C) solution of 2S-hydroxy-3R-(4-trifluoromethoxy-benzyl)-succinic acid dimethyl ester (1.50 g, 4.45 mmol) in MeOH/water (3:1, 28 ml) was added lithium hydroxide (617 mg, 14.7 mmol, 3.3 eq.). The reaction mixture was stirred at RT for 16 hrs. The reaction was quenched by addition of HCl 1N (5 ml) and MeOH was removed under reduced pressure. The extraction was carried out with AcOEt (10 ml). The organic layer was washed with HCl 1N (10 ml), water (10 ml) and finally with brine (10 ml). The organic layer was dried over MgSO$_4$. Solvent was removed under reduced pressure to give the expected 2S-hydroxy-3R-(4-trifluoromethoxy-benzyl)-succinic acid as a clear oil (1.36 g, 99% yield).

$^1$H-NMR; delta (CDCl$_3$): 7.32 (2H, d, J=8.4 Hz), 7.19 (2H, d, J=8.4 Hz), 4.08 (1H, d, J=6.5 Hz), 3.25 (2H, m), 3.05 (1H, m).

LRMS: +ve ion 331 (M+Na), −ve ion 307 (M−H).

Step C: 2R-(2,2-dimethyl-5-oxo-[1,3]dioxolan-4S-yl)-3-(4-trifluoromethoxy-phenyl)-propionic acid.

To a solution of 2S-hydroxy-3R-(4-trifluoromethoxy-benzyl)-succinic acid (1.36 g, 4.4 mmol) in acetone (10 ml) under an inert atmosphere were added dimethoxy propane (923 µl, 7.5 mmol, 1.7 eq.) and copper chloride (59 mg, 0.44 mmol, 0.1 eq.). The reaction mixture was stirred at RT for 16 hrs. The solvent was then removed under vacuo to give 2R-(2,2-dimethyl-5-oxo-[1,3]dioxolan-4S-yl)-3-(4-trifluoromethoxy-phenyl)-propionic acid (1.08 g, 70% yield).

¹H-NMR; delta (CDCl₃): 7.29 (2H, d, J=8.7 Hz), 7.14 (2H, d, J=8.4 Hz), 4.30 (1H, d, J=6.2 Hz), 3.21 (2H, m), 3.0 (1H, m), 1.61 (3H, s), 1.52 (3H, s).

LRMS: +ve ion 371 (M+Na), −ve ion 347 (M−H).

Step D: 2R-(2,2-dimethyl-5-oxo-[1,3]dioxolan-4S-yl)-3-(4-trifluoromethoxy-phenyl)-propionic acid pentafluorophenyl ester.

To a cold (0 C) solution of 2R-(2,2-dimethyl-5-oxo-[1,3]dioxolan-4S-yl)-3-(4-trifluoromethoxy-phenyl)-propionic acid (1.08 g, 3.1 mmol) and pentafluoro phenol (685 mg, 3.7 mmol, 1.2 eq.) in CH₂Cl₂ (10 ml) was added WSC (714 mg, 3.7 mmol, 1.2 eq.). The reaction mixture was allowed to warm to RT overnight. CH₂Cl₂ was removed under vacuo and the resulting crude reaction mixture was dissolved in AcOEt (80 ml). The organic layer was washed with water (20 ml), NaHCO₃ sat (10 ml) and finally with brine (10 ml). Solvent was removed under reduced pressure to give an oil which was purified by flash chromatography to furnish the expected 2R-(2,2-dimethyl-5-oxo-[1,3]dioxolan-4S-yl)-3-(4-trifluoromethoxy-phenyl)-propionic acid pentafluorophenyl ester (254 mg, 16% yield).

¹H-NMR; delta (CDCl₃): 7.29 (2H, bd, J=9.3 Hz), 7.21 (2H, bd, J=8.7 Hz), 4.45 (1H, d, J=6.2 Hz), 3.51 (1H, m), 3.3 (2H, m), 1.65 (3H, s), 1.58 (1H, s).

LRMS: +ve ion 537 (M+Na).

Step E: 5S-[2-(4-benzo[1,3]dioxol-5-ylmethyl-piperazin-1-yl]-2-oxo-1R-(4-trifluoromethoxy-benzyl)-ethyl]-2,2-dimethyl-[1,3]dioxolan-4-one.

To a solution of 2-(2,2-dimethyl-5-oxo-[1,3]dioxolan-4S-yl)-3R-(4-trifluoromethoxy-phenyl)-propionic acid pentafluorophenyl ester (59 mg, 0.11 mmol) in CH₂Cl₂ (10 ml) was added 1-benzo[1,3]dioxol-5-ylmethyl-piperazine (28 mg, 0.13 mmol, 1.1 eq.). The reaction mixture was stirred for 16 hrs and the solvent was removed under vacuo. The crude was taken-up in AcOEt (50 ml) and washed with water (10 ml), then with NaHCO₃ sat (10 ml) and finally with brine (10 ml). The solvent was dried over MgSO₄ and removed under reduced pressure to give an oil which was purified by preparative reverse phase chromatography to afford the expected 5S-[2-(4-benzo[1,3]dioxol-5-ylmethyl-piperazin-1-yl)-2-oxo-1R-(4-trifluoromethoxy-benzyl)-ethyl]-2,2-dimethyl-[1,3]dioxolan-4-one.

¹H-NMR; delta (CD₃OD): 7.27-7.12 (4H, m), 6.78-6.62 (3H, m), 5.93 (2H, s), 4.57 (1H, d, J=6.6 Hz), 3.85-2.9 (10H, m), 2.44-2.21 (2H, m), 2.05-1.91 (1H, m), 1.69-1.42 (6H, m).

LRMS: +ve ion 551 (M+H).

Step F: 4-(4-benzo[1,3]dioxol-5-ylmethyl-piperazin-1-yl)-2S,N-dihydroxy-4-oxo-3R-(4-trifluoromethoxy-benzyl)-butyramide.

To a solution of 5S-[2-(4-benzo[1,3]dioxol-5-ylmethyl-piperazin-1-yl)-2-oxo-1R-(4-trifluoromethoxy-benzyl)-ethyl]-2,2-dimethyl-[1,3]dioxolan-4-one (26 mg, 0.047 mmol) in i-PrOH (2 ml), was added an aqueous solution of hydroxylamine (50%, 16 μl, 0.24 mmol, 5 eq.). The reaction mixture was allowed to stir at RT for 16 hrs. The solvent was removed under reduced pressure to yield an oil which was purified by preparative reverse phase chromatography to give the required 4-(4-Benzo[1,3]dioxol-5-ylmethyl-piperazin-1-yl)-2S,N-dihydroxy-4-oxo-3R-(4-trifluoromethoxy-benzyl)-butyramide.

¹H-NMR; delta (CD₃OD): 7.32-7.15 (4H), 6.79-6.65 (4H, m), 5.90 (2H, s), 4.13 (1H, d, J=6.8 Hz), 3.75-3.35 (4H, m), 3.30 (2H, s), 3.0-2.8 (4H, m), 2.5-2.25 (2H, m), 1.90 (1H, m).

LRMS: +ve ion 526 (M+H); −ve ion 524 (M−H).

EXAMPLE 30

3R-benzyl-2S,N-dihydroxy-4-morpholin-4-yl-4-oxo-butyramide

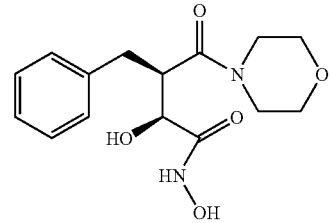

The compound of example 30 was prepared by the method of example 29 according to scheme 4, and using the benzyl bromide in step A and morpholine in step E.

¹H-NMR; delta (CD₃OD): 7.32-7.18 (5H, m), 4.16 (1H, d, J=6.7 Hz), 3.59-2.67 (11H, m).

LRMS: +ve ion 331 (M+Na); −ve ion 307 (M−H).

EXAMPLE 31

3R-(4-Benzyloxy-benzyl)-2S,N-dihydroxy-4-oxo-4-piperidin-1-yl-butyramide

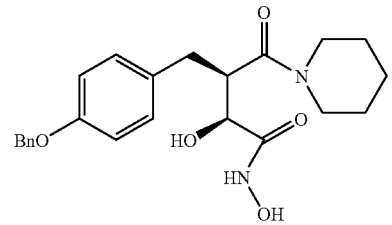

The compound of example 31 was prepared by the method of example 29 according to scheme 4, and using the 1-benzyloxy-4-bromomethyl-benzene in step A and piperidine in step E.

¹H-NMR; delta(MeOD): 7.41-7.26 (5H, m), 7.10-6.87 (4H, m), 5.05 (2H, s), 4.11 (1H, d, J=J 6.1 Hz), 3.57-3.48 (2H, m), 3.24-3.09 (3H, m), 2.89-2.69 (2H, m), 1.41-1.17 (5H, m) and 0.72-0.67 (1H, m).

LRMS: +ve ion 435 (M+Na); −ve ion 411 (M−H).

EXAMPLE 32

2S,N-dihydroxy-3R-(4-hydroxy-benzyl)-4-oxo-4-piperidin-1-yl-butyramide

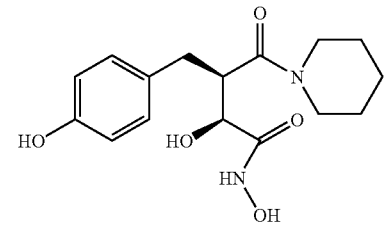

Example 32 was prepared as outlined in Scheme 5 using procedures described below.

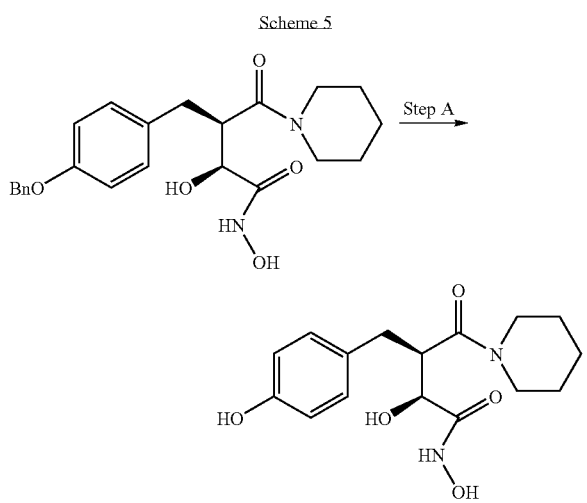

Reagents and conditions: A: H$_2$, Pd/C, MeOH

Step A: 2S,N-dihydroxy-3R-(4-hydroxy-benzyl)-4-oxo-4-piperidin-1-yl-butyramide.

To a solution of 2S,N-dihydroxy-3R-(4-hydroxy-benzyl)-4-oxo-4-piperidin-1-yl-butyramide (14 mg, 3.5·10$^{-5}$ mol) in MeOH (5 ml) under an inert atmosphere, was added 10% Pd/C (1 mg). H$_2$ was then bubbled through the resulting suspension for 2 hrs. Pd/C was filtered off and the solvent was removed under reduced pressure to give 2S,N-dihydroxy-3R-(4-hydroxy-benzyl)-4-oxo-4-piperidin-1-yl-butyramide (10 mg, quant.).

$^1$H-NMR; delta (MeOD): 7.02-6.67 (4H, 2d, J=8.4 Hz and J 8.4 Hz), 4.12 (1H, d, J=6.0 Hz), 3.65-3.48 (2H, m), 3.27-3.12 (3H, m), 2.87-2.68 (2H, m), 1.47-1.26 (5H, m) and 0.83-0.78 (1H, m).

LRMS: +ve ion 345 (M+Na); −ve ion 321 (M−H).

EXAMPLE 33

4-(4-benzo[1,3]dioxol-5-ylmethyl-piperazin-1-yl)-3R-(4-benzyloxy-benzyl)-2S,N-dihydroxy-4-oxo-butyramide

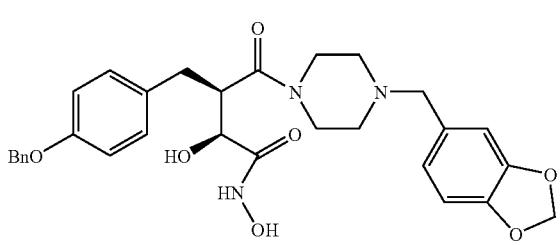

The compound of example 33 was prepared by the method of example 29 according to scheme 4, and using the 1-benzyloxy-4-bromomethyl-benzene in step A.

$^1$H-NMR; delta (DMSO): 9.80 (1H, s), 8.88 (1H, s), 7.48-7.31 (5H, m), 7.04-6.90 (4H, m), 6.82-6.77 (2H, m), 6.67-6.62 (1H, m), 5.98 (2H, s), 5.45 (1H, d), 5.09 (2H, s), 3.91 (1H, m), 3.56-3.44 (2H, m), 3.20-3.08 (6H, m), 2.78-2.60 (1H, m), 2.30-2.08 (2H, m), 1.92-1.83 (1H, m) and 1.42-1.30 (1H, m).

LRMS: +ve ion 548 (M+H); −ve ion 546 (M−H).

EXAMPLE 34

6-(3,5-bis-trifluoromethyl-phenyl)-2S-hydroxy-3R-(morpholine-4-carbonyl)-hexanoic acid hydroxyamide The compounds of Examples 34-38 were prepared by the method of Example 1 according to scheme 1, where ArBr in Step B was 1-bromomethyl-3,5-bis-trifluoromethyl-benzene by parallel synthesis and using the appropriate amine in Step G. The products were purified by preparative HPLC.

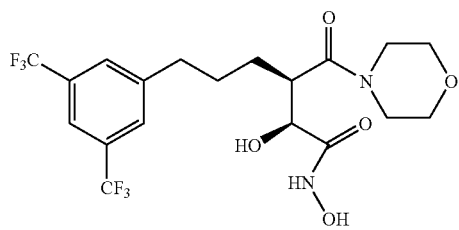

$^1$H-NMR; delta (CD$_3$OD): 7.79 (2H, s), 7.77 (1H, s), 4.07 (1H, d, J=6.8 Hz), 3.19-3.76 (9H, m), 2.73-2.98 (2H, m), 1.52-1.88 (4H, m).

LRMS: +ve ion 473 (M+H), 495 (M+Na); −ve ion 471 (M−H).

EXAMPLE 35

3R-(4-benzyl-piperidine-1-carbonyl)-6-(3,5-bis-trifluoromethyl-phenyl)-2S-hydroxy-hexanoic acid hydroxyamide

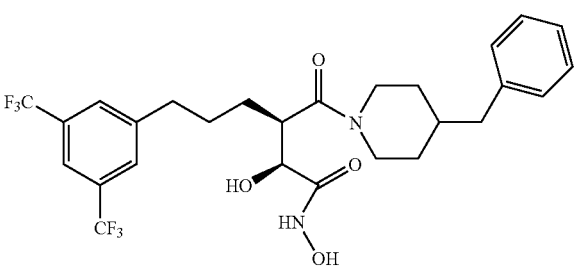

LRMS: +ve ion 561 (M+H), 583 (M+Na); −ve ion 559 (M−H).

EXAMPLE 36

6-(3,5-bis-trifluoromethyl-phenyl)-2S-hydroxy-3R-(4-pyridin-2-yl-piperazine-1-carbonyl)-hexanoic acid hydroxyamide

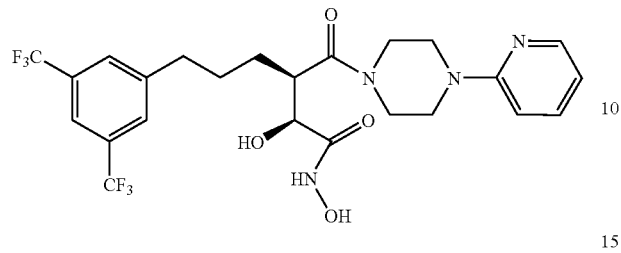

LRMS: +ve ion 549 (M+H); −ve ion 547 (M−H).

EXAMPLE 37

6-(3,5-bis-trifluoromethyl-phenyl)-3R-(6,7-dimethoxy-3,4-dihydro-1H-isoquinoline-2-carbonyl)-2S-hydroxy-hexanoic acid hydroxyamide

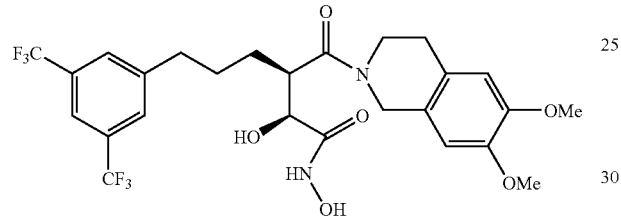

LRMS: +ve ion 601 (M+Na); −ve ion 577 (M−H).

EXAMPLE 38

6-(3,5-bis-trifluoromethyl-phenyl)-2S-hydroxy-3R-(pyrrolidine-1-carbonyl)-hexanoic acid hydroxyamide

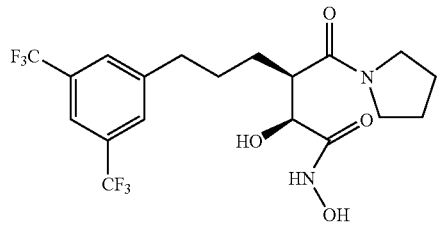

¹H-NMR; delta (CD₃OD): 7.84 (2H, s), 7.79 (1H, s), 4.06 (1H, d, J=6.6 Hz), 3.71-3.81 (1H, m), 3.10-3.54 (5H, m), 2.75-2.83 (1H, m), 1.51-1.98 (7H, m).

LRMS: +ve ion 479 (M+Na); −ve ion 455 (M−H).

EXAMPLE 39

3R-(2S-benzyl-4-methyl-piperazine-1-carbonyl)-6-(4-ethoxy-phenyl)-2S-hydroxy-hexanoic acid hydroxyamide

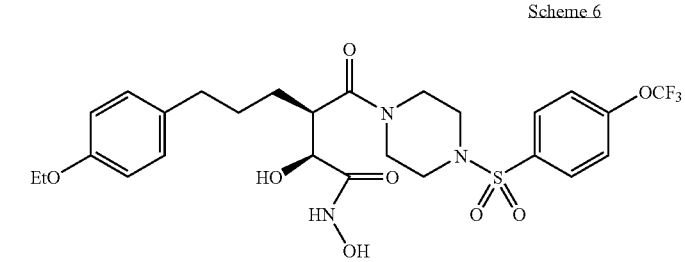

The compound of example 39 was prepared by the method of example 1 according to scheme 1, and using the appropriate piperazine (synthesised according to the procedure described in J. Heterocyclic Chem, 28, 1219-1224, 1991; in Step A. The product was purified by preparative HPLC.

LRMS: +ve ion 484 (M+H).

EXAMPLE 40

6-(4-ethoxy-phenyl)-2S-hydroxy-3R-[4-(4-trifluoromethoxy-benzenesulfonyl)-piperazine-1-carbonyl]-hexanoic acid hydroxyamide Scheme 6

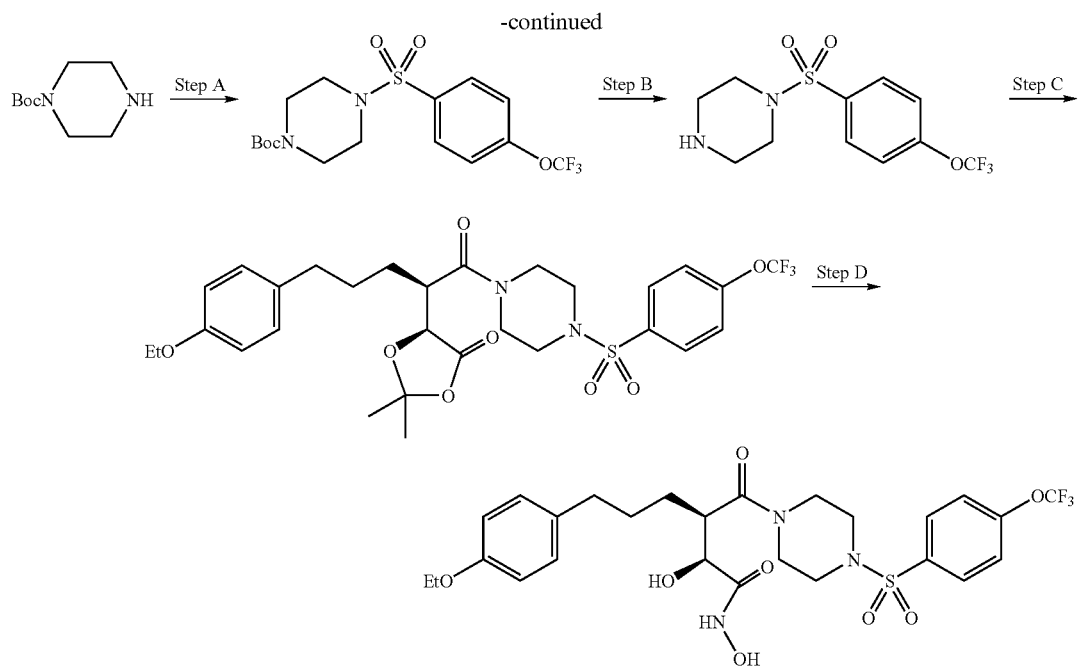

Reagents and conditions: A: RSO₂Cl 1.2 eq., NEt₃ 1.4 eq., CH₂Cl₂;
B: TFA/CH₂Cl₂; C: LHS, EDAC, HOAt, CH₂Cl₂; D: H₂NOH aq., iPrOH Example 40 was prepared as outlined in Scheme 6 using procedures described below.

Step A: 4-(4-trifluoromethoxy-benzenesulfonyl)-piperazine-1-carboxylic acid tert-butyl ester.

To a solution of piperazine-1-carboxylic acid tert-butyl ester (521 mg, 2.8 mmol) in DCM (6 ml) was added NEt₃ (547 µl, 3.92 mmol, 1.4 eq.) and 4-trifluoromethoxy-benzenesulfonyl chloride (880 mg, 3.36 mmol, 1.2 eq.). The reaction mixture was stirred at room temperature for 12 hrs. The excess of sulfonyl chloride was quenched by addition of trisamine resin (150 mg), and subsequent stirring for 2 hrs. The resin was then filtered off, and NaHCO₃ sat (5 ml) was added. Filtration of the resulting mixture through hydrophobic catridge and subsequent removal of the solvent under reduced pressure afforded the desired 4-(4-trifluoromethoxy-benzenesulfonyl)-piperazine-1-carboxylic acid tert-butyl ester in quantitative yield.

Step B: 1-(4-trifluoromethoxy-benzenesulfonyl)-piperazine.

To a cold (0 C) solution of 4-(4-trifluoromethoxy-benzenesulfonyl)-piperazine-1-carboxylic acid tert-butyl ester (1.15 g, 2.8 mmol) in DCM (3 ml) was added TFA (2 ml). The resulting solution was stirred for 1 hr. Solvent was then removed under reduced pressure. The crude solid was taken-up in AcOEt (15 ml) and washed with NaHCO₃ sat (2×5 ml), water (5 ml) and finally with brine (5 ml). The organic layer was dried over MgSO₄ and the solvent was removed under vacuo to yield the desired 1-(4-trifluoromethoxy-benzenesulfonyl)-piperazine as a white solid (753 mg, 87% yield).

¹H-NMR; delta (CDCl₃): 7.80 (2H, m), 7.38 (2H, m), 3.01 (8H, m).

LRMS: +ve ion 311 (M+H).

Step C: 5-{4-(4-ethoxy-phenyl)-1-[4-(4-trifluoromethoxy-benzenesulfonyl)-piperazine-1-carbonyl]-butyl}-2,2-dimethyl-[1,3]dioxolan-4-one.

To a cold (0 C) solution of 2R-(2,2-dimethyl-5-oxo-[1,3]dioxolan-4S-yl)-5-(4-ethoxy-phenyl)-pentanoic acid (91 mg, 0.27 mmol), 1-(4-trifluoromethoxy-benzenesulfonyl)-piperazine (100 mg, 0.325 mmol, 1.2 eq.) in DCM (6 ml), was added WSCDI (62 mg, 0.325 mmol, 1.2 eq.) and HOAt (cat). The reaction mixture was stirred for 16 hrs allowing the temperature to raise to 20 C. DCM was then removed under reduced pressure, and the resulting crude reaction mixture was taken-up in AcOEt (30 ml). The organic layer was washed with water (2×10 ml) and with brine (10 ml). The organic layer was dried over MgSO₄ and the solvent was removed under vacuo to yield the desired 5-{4-(4-ethoxy-phenyl)-1-[4-(4-trifluoromethoxy-benzenesulfonyl)-piperazine-1-carbonyl]-butyl}-2,2-dimethyl-[1,3]dioxolan-4-one (170 mg, quant.).

LRMS: +ve ion 629 (M+H), 651 (M+Na).

Step D: 6-(4-ethoxy-phenyl)-2S-hydroxy-3R-[4-(4-trifluoromethoxy-benzenesulfonyl)-piperazine-1-carbonyl]-hexanoic acid hydroxyamide.

To a solution of 5-{4-(4-ethoxy-phenyl)-1-[4-(4-trifluoromethoxy-benzenesulfonyl)-piperazine-1-carbonyl]-butyl}-2,2-dimethyl-[1,3]dioxolan-4-one (170 mg, 0.27 mmol) in iPrOH (5 ml) was added H₂NHOH$_{aq}$ (90 µl, 1.35 mmol, 5 eq.). The reaction mixture was stirred for 12 hrs and the solvent was remove under vacuo. The crude reaction mixture was purified through preparative HPLC to give the expected 6-(4-ethoxy-phenyl)-2S-hydroxy-3R-[4-(4-trifluoromethoxy-benzenesulfonyl)-piperazine-1-carbonyl]-hexanoic acid hydroxyamide.

¹H-NMR; delta (CDCl₃): 7.79 (2H, m), 7.38 (2H, m), 7.01 (2H, m), 6.80 (2H, m), 4.06 (2H, q), 3.90 (1H, m), 3.64 (1H, m), 3.43-3.20 (3H, m), 3.19-3.00 (2H, t), 2.91-2.70 (2H, dt), 2.5 (2H, t), 1.8-1.5 (2H, m), 1.41 (3H, t).

LRMS: +ve ion 604 (M+H), 651 (M+Na), −ve ion (602 (M−H).

EXAMPLE 41

6-(4-ethoxy-phenyl)-2S-hydroxy-3R-[4-(toluene-4-sulfonyl)-piperazine-1-carbonyl]-hexanoic acid hydroxyamide

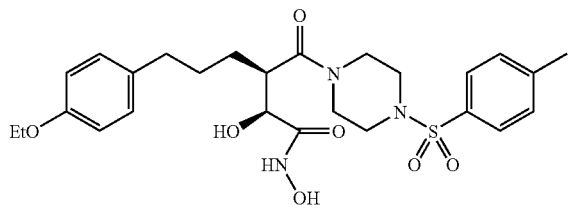

The compound of example 41-46 were prepared by the method of example 40 according to scheme 6, and using the appropriate sulfonyl chloride in step A.

LRMS: +ve ion 534 (M+H), −ve ion 532 (M−H).

EXAMPLE 42

3R-[4-(5-bromo-thiophene-2-sulfonyl)-piperazine-1-carbonyl]-6-(4-ethoxy-phenyl)-2S-hydroxy-hexanoic acid hydroxyamide

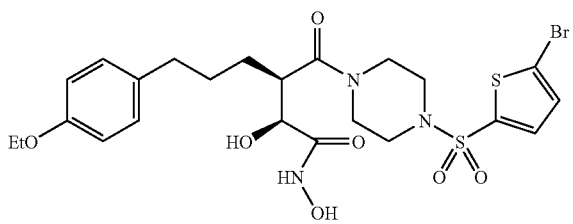

LRMS: +ve ion 605 (M+H), −ve ion 603 (M−H).

EXAMPLE 43

3R-[4-(5-benzenesulfonyl-thiophene-2-sulfonyl)-piperazine-1-carbonyl]-6-(4-ethoxy-phenyl)-2S-hydroxy-hexanoic acid hydroxyamide

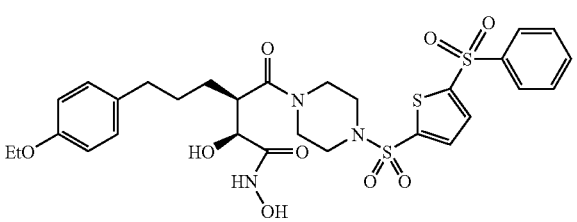

LRMS: +ve ion 666 (M+H), −ve ion 664 (M−H).

EXAMPLE 44

3R-[4-(4-butoxy-benzenesulfonyl)-piperazine-1-carbonyl]-6-(4-ethoxy-phenyl)-2S-hydroxy-hexanoic acid hydroxyamide

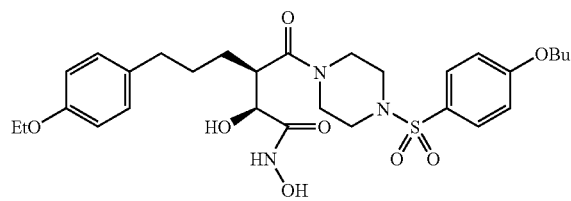

LRMS: +ve ion 592 (M+H), −ve ion 590 (M−H).

EXAMPLE 45

6-(4-ethoxy-phenyl)-2S-hydroxy-3R-[4-(4-methoxy-2,3,6-trimethyl-benzenesulfonyl)-piperazine-1-carbonyl]-hexanoic acid hydroxyamide

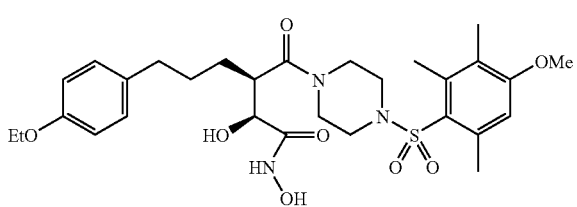

LRMS: +ve ion 592 (M+H), −ve ion 590 (M−H).

EXAMPLE 46

3R-[4-(3,4-dimethoxy-benzenesulfonyl)-piperazine-1-carbonyl]-6-(4-ethoxy-phenyl)-2S-hydroxy-hexanoic acid hydroxyamide

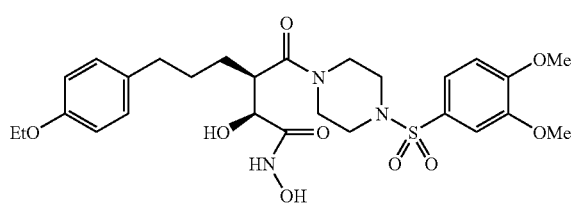

LRMS: +ve ion 580 (M+H), −ve ion 578 (M−H).

The compounds of Examples 47-50 were prepared by the method of Example 1 by parallel synthesis, using the appropriate aryl bromide in Step B, and the appropriate amine in Step G. The products were purified by preparative HPLC

EXAMPLE 47

6-(4-methoxy-phenyl)-2S-hydroxy-3R-[4-(2-fluoro-phenyl)-piperazine-1-carbonyl]-hexanoic acid hydroxyamide

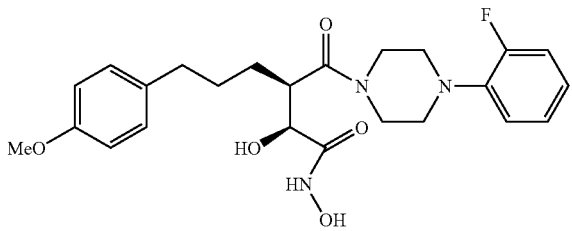

$^1$H-NMR; delta (MeOD): 7.20-7.00 (6H, m), 6.85 (2H, m), 4.15-4.10 (1H, m), 3.95-3.70 (6H, m), 3.45-3.35 (4H, m), 3.20-2.95 (3H, m), 2.65-2.55 (2H, m), 1.80-1.55 (3H, m).
LRMS: +ve ion 460 (M+H); −ve ion 458 (M−H).

EXAMPLE 48

6-(4-methoxy-phenyl)-2S-hydroxy-3R-(4-pyridin-2-yl-piperazine-1-carbonyl)-hexanoic acid hydroxyamide

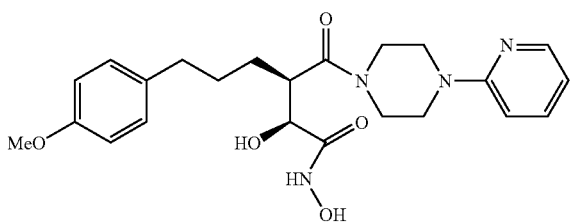

$^1$H-NMR; delta (MeOD): 8.15-8.10 (1H, m), 7.65-7.55 (1H, m), 7.15-7.05 (2H, m), 6.90-6.80 (3H, m), 6.80-6.70 (1H, m), 4.20-4.10 (1H, m), 3.95-3.35 (13H, m), 2.65-2.55 (2H, m), 1.80-1.55 (3H, m).
LRMS: +ve ion 443 (M+H).

EXAMPLE 49

6-(4-fluoro-phenyl)-3R-[4-(2-fluoro-phenyl)-piperazine-1-carbonyl]-2S-hydroxy-hexanoic acid hydroxyamide

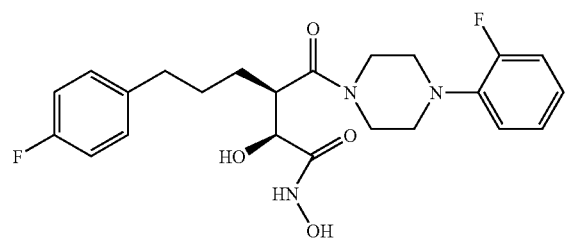

$^1$H-NMR; delta (MeOD): 7.2-6.9 (8H, m), 4.05 (1H, d), 3.9-3.6 (4H, m), 3.35 (2H, m), 3.1-2.9 (3H, m), 2.55 (2H, t), 1.8-1.5 (3H, m), 1.15 (1H, t).
LRMS: +ve ion 448 (M+H).

EXAMPLE 50

6-(4-fluoro-phenyl)-2S-hydroxy-3R-(4-pyridin-2-yl-piperazine-1-carbonyl)-hexanoic acid hydroxyamide

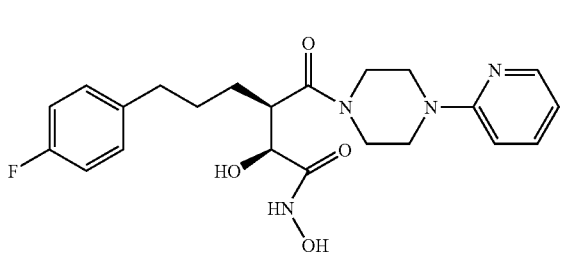

$^1$H-NMR; delta (MeOD): 8.1 (1H, d), 7.55 (1H, t), 7.15 (2H, m), 6.9 (2H, m), 6.8 (1H, d), 6.7 (1H, m), 4.05 (1H, d), 3.85 (2H, m), 3.7-3.3 (6H, m), 3.05 (1H, t), 2.55 (2H, t), 1.8 (4H, m), 1.15 (1H, t).
LRMS: +ve ion 431 (M+H).

EXAMPLE 51

3R-(4-benzyl-2S-methyl-piperazine-1-carbonyl)-6-(4-ethoxy-phenyl)-2S-hydroxy-hexanoic acid hydroxyamide

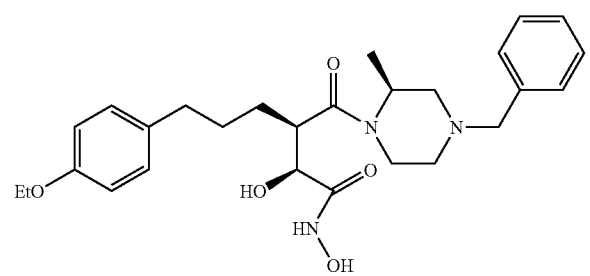

Example 51 was prepared as outlined in Scheme 7 using procedures described below.

The piperazine intermediates used in step A of scheme 7 were prepared according to the procedures described in Journal of Organic Chemistry, 60, 4177-4183, 1995.

Scheme 7

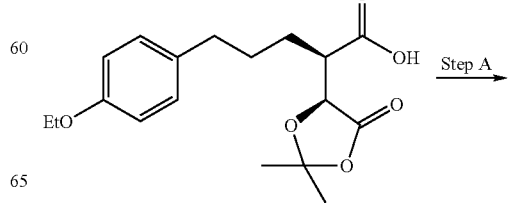

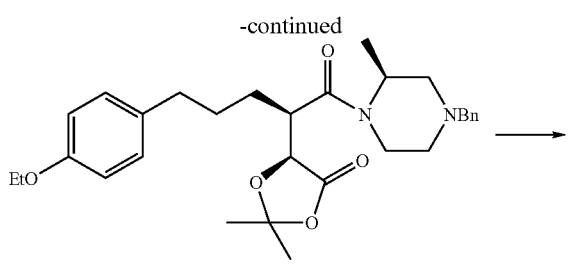

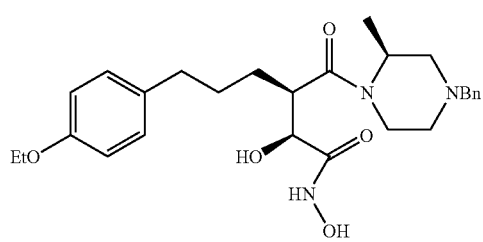

Reagents and conditions: Step A: 1-benzyl-3S-methyl-piperazine, WSC, HOAt, CH$_2$Cl$_2$; Step B: H$_2$NOH$_{aq}$, iPrOH Step A: 5S-[1-(4-benzyl-2S-methyl-piperazine-1-carbonyl)-4R-(4-ethoxy-phenyl)-butyl]-2,2-dimethyl-[1,3]dioxolan-4-one.

To a cold (0 C) mixture of 2R-(2,2-dimethyl-5-oxo-[1,3]dioxolan-4S-yl)-5-(4-ethoxy-phenyl)-pentanoic acid (80 mg, 2.38·10$^{-4}$ mol) and 1-benzyl-3S-methyl-piperazine (54 mg, 2.84·10$^{-4}$ mol, 1.2 eq), were added WSC (55 mg, 2.84·10$^{-4}$ mol, 1.2 eq) and HOAt (cat). The reaction mixture was then stirred at RT for 16 hrs before being diluted by addition of 5 ml of CH$_2$Cl$_2$. The organic layer was washed with water (3 ml) and then dried over MgSO$_4$. The solvent was removed under reduced pressure to afford the desired 5S-[1-(4-benzyl-2S-methyl-piperazine-1-carbonyl)-4R-(4-ethoxy-phenyl)-butyl]-2,2-dimethyl-[1,3]dioxolan-4-one which was used in the next step without any further purification.

Step B: 3R-(4-benzyl-2S-methyl-piperazine-1-carbonyl)-6-(4-ethoxy-phenyl)-2S-hydroxy-hexanoic acid hydroxyamide.

To a cold (0 C) solution of 5S-[1-(4-benzyl-2S-methyl-piperazine-1-carbonyl)-4R-(4-ethoxy-phenyl)-butyl]-2,2-dimethyl-[1,3]dioxolan-4-one (120 mg, 2.38·10$^{-4}$ mol) in iPrOH (4 ml), was added H$_2$NOH (100 ml, 1.19·10$^{-3}$ mol, 5 eq). The reaction mixture was stirred at RT for 5 hrs and the solvent was removed under reduced pressure. The crude oil was purified by prep. HPLC to yield the expected 3R-(4-benzyl-2S-methyl-piperazine-1-carbonyl)-6-(4-ethoxy-phenyl)-2S-hydroxy-hexanoic acid hydroxyamide as a white solid.

LRMS: +ve ion 484 (M+H).

The compound of example 52-61 were prepared by the method of example 51 according to scheme 7, and using the appropriate piperazines.

EXAMPLE 52

3R-(4-benzyl-2S-methyl-piperazine-1-carbonyl)-6-(4-methoxy-phenyl)-2S-hydroxy-hexanoic acid hydroxyamide

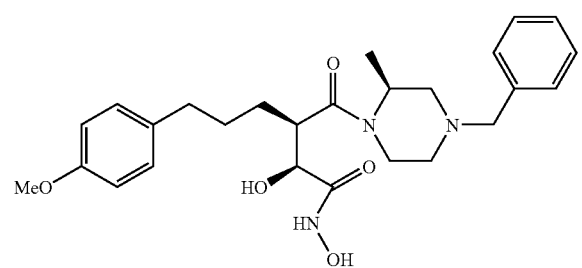

LRMS: +ve ion 470 (M+H).

EXAMPLE 53

3R-(4-benzyl-2S-1-butyl-piperazine-1-carbonyl)-6-(4-methoxy-phenyl)-2S-hydroxy-hexanoic acid hydroxyamide

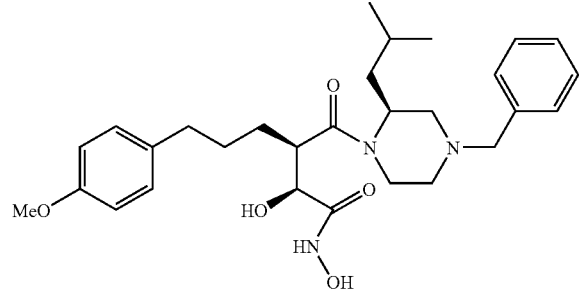

LRMS: +ve ion 512 (M+H).

EXAMPLE 54

3R-(4-benzyl-2S-methyl-piperazine-1-carbonyl)-6-(4-fluoro-phenyl)-2S-hydroxy-hexanoic acid hydroxyamide

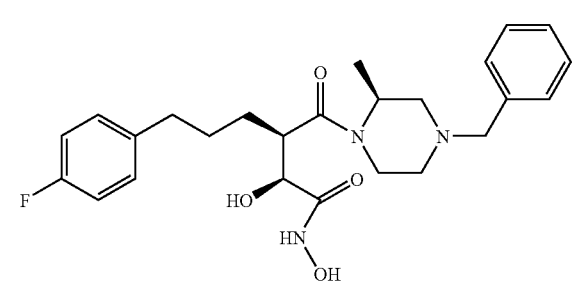

LRMS: +ve ion 458 (M+H).

EXAMPLE 55

3R-(4-benzyl-2S-1-butyl-piperazine-1-carbonyl)-6-(4-fluoro-phenyl)-2S-hydroxy-hexanoic acid hydroxyamide

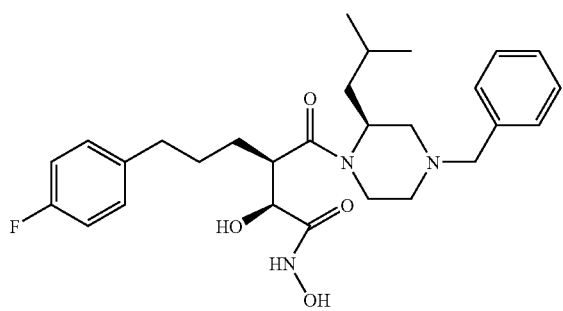

LRMS: +ve ion 500 (M+H).

EXAMPLE 56

4-[5-(4-ethoxy-phenyl)-2R-(1S-hydroxy-hydroxycarbamoyl-methyl)-pentanoyl]-2S-methyl-piperazine-1-carboxylic acid tert-butyl ester

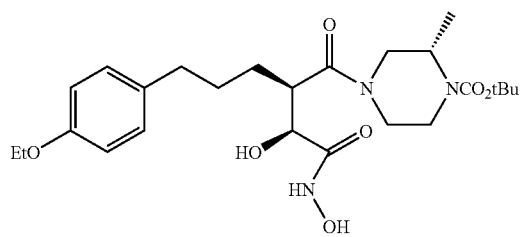

LRMS: +ve ion 494 (M+H).

EXAMPLE 57

4-[5-(4-ethoxy-phenyl)-2R-(1S-hydroxy-hydroxycarbamoyl-methyl)-pentanoyl]-2S-1-butyl-piperazine-1-carboxylic acid tert-butyl ester

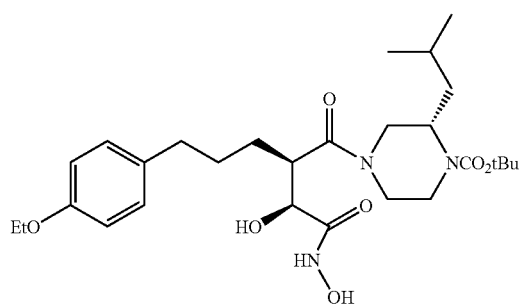

LRMS: +ve ion 536 (M+H).

EXAMPLE 58

4-[5-(4-methoxy-phenyl)-2R-(1S-hydroxy-hydroxy-carbamoyl-methyl)-pentanoyl]-2S-methyl-piperazine-1-carboxylic acid tert-butyl ester

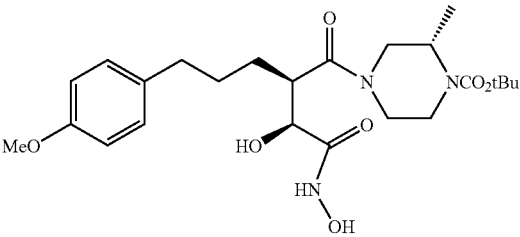

LRMS: +ve ion 480 (M+H).

EXAMPLE 59

4-[5-(4-methoxy-phenyl)-2R-(1S-hydroxy-hydroxy-carbamoyl-methyl)-pentanoyl]-2S-1-butyl-piperazine-1-carboxylic acid tert-butyl ester

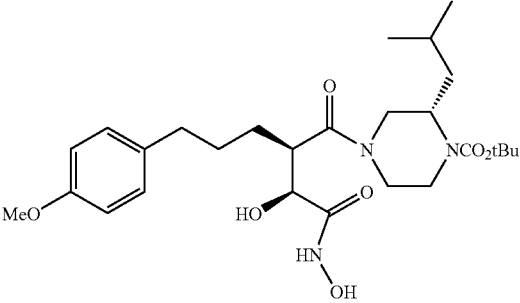

LRMS: +ve ion 522 (M+H).

EXAMPLE 60

4-[5-(4-fluoro-phenyl)-2R-(1S-hydroxy-hydroxycarbamoyl-methyl)-pentanoyl]-2S-methyl-piperazine-1-carboxylic acid tert-butyl ester

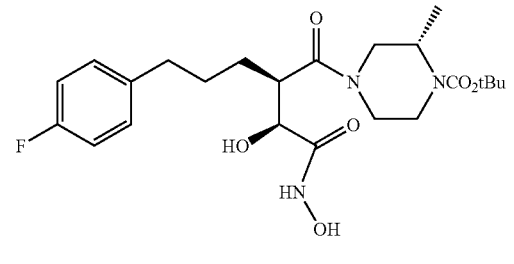

LRMS: +ve ion 468 (M+H).

EXAMPLE 61
4-[5-(4-fluoro-phenyl)-2R-(1S-hydroxy-hydroxycarbamoyl-methyl)-pentanoyl]-2S-i-butyl-piperazine-1-carboxylic acid tert-butyl ester LRMS: +ve ion 510 (M+H).
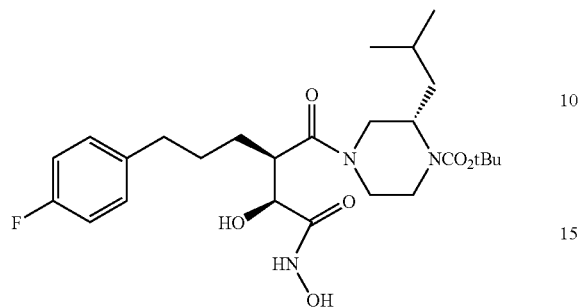
EXAMPLE 62
6-(4-ethoxy-phenyl)-2S-methoxy-3R-[4-(2-fluoro-phenyl)-piperazine-1-carbonyl]-hexanoic acid hydroxyamide
Scheme 1
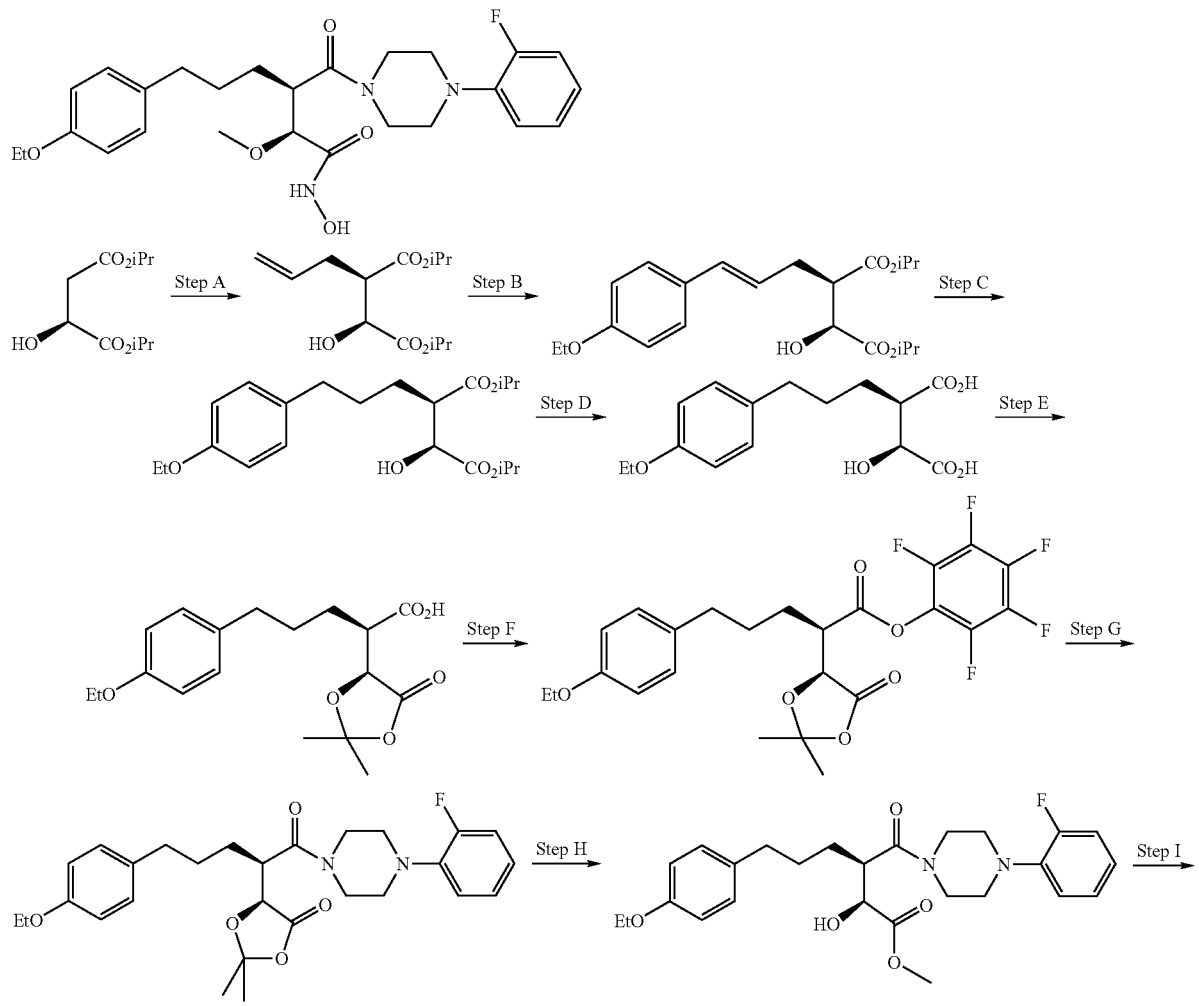

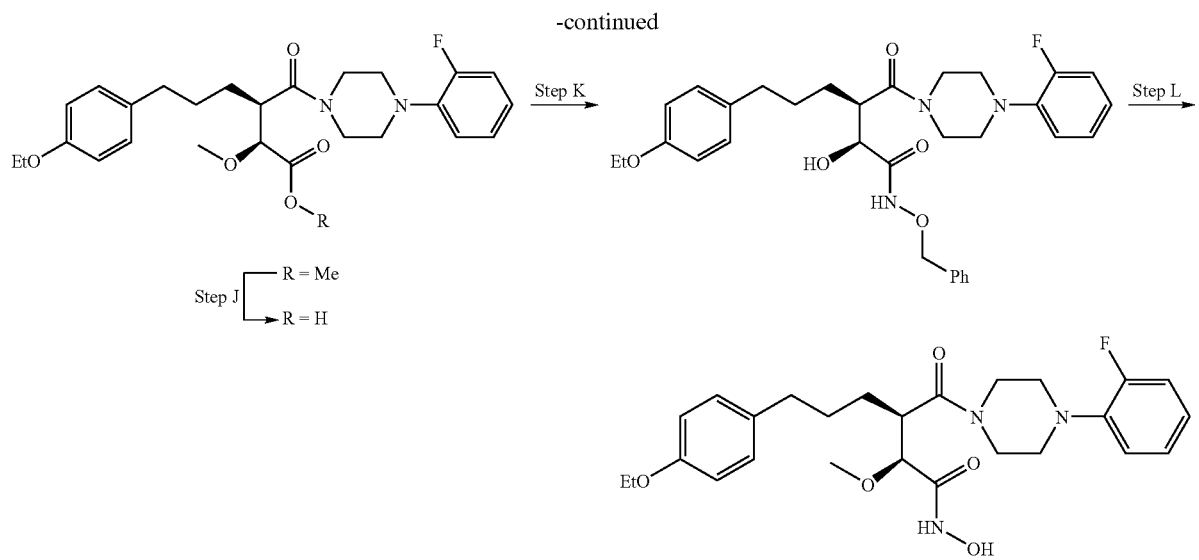

Reagents and conditions. A: LiHMDS, AllBr, THF, −78 C. to RT; B: ArBr, P(o-Tol)₃, Pd(OAc)₂, NEt₃, CH₃CN; C: 10% Pd/C, H₂, MeOH; D: LiOH, MeOH, H₂O; E: CuCl₂, dimethoxypropane, acetone; F: pentafluorophenol, WSCDI, HOAt, CH₂Cl₂; G: 1-(2-fluoro-phenyl)-piperazine, NEt₃, CH₂Cl₂; H: thionyl chloride, methanol; I: NaH, methyl iodide, DMF; J: NaOH, MeOH, water; K: BnONH2, WSC, HOBt, DMF; L: H2, Pd/C, ethanol The compound of this Example 62 was prepared as outlined in Scheme 1 using procedures described below.

Step A: 2R-allyl-3S-hydroxy-succinic acid diisopropylester.

To a cold (−78 C) solution of 2S-hydroxy-succinic acid diisopropyl ester (19.70 ml, 95 mmol) in THF (35 ml) was added LiHMDS (200 ml, 0.2 mol, 2.1 eq.) dropwise. The reaction mixture was stirred at −78 C for two hours and then at −30 C for 30 min. The reaction mixture was then cooled to −78 C and allyl bromide (12.36 ml, 0.14 mol, 1.5 eq.) added dropwise. The reaction mixture was then allowed to warm to RT overnight. It was poured into a saturated solution of NH₄Cl/ice (200 ml). Extraction with AcOEt (3×200 ml) followed by a wash with water (50 ml) and with brine (50 ml) afforded a yellow oil after removal of the solvents under vacuo. Purification by flash chromatography gave 2R-allyl-3S-hydroxy-succinic acid diisopropylester as a colourless oil (7.76 g, de=80%, 40% yield).

¹H-NMR; delta (CDCl₃): 5.77-5.88 (1H, m), 4.98-5.21 (4H, m), 4.22 (1H, brs), 3.18 (1H, brs), 2.87-2.94 (1H, m), 2.56-2.65 (1H, m), 2.40-2.48 (1H, m), 1.29 (6H, d, J=6.3 Hz), 1.22 (6H, d, J=6.3 Hz).

LRMS: +ve ion 281 (M+Na).

Step B: 2R-[3-(4-ethoxy-phenyl)-allyl]-3S-hydroxy-succinic acid diisopropyl ester.

To a solution of 2R-allyl-3S-hydroxy-succinic acid diisopropylester (4.79 g, 18.5 mmol), 4-bromo phenetole (3.19 ml, 22.2 mmol, 1.2 eq.) and NEt₃ (6.22 ml, 44.6 mmol, 2.4 eq.) in CH₃ CN (40 ml), was added a sonicated (for 2 min) suspension of P(O-Tol)₃ (0.57 g, 2.22 mmol, 0.1 eq.) and Pd(OAc)₂ (209 mg, 5%) in CH₃ CN (5 ml). The reaction mixture was heated to reflux for 2 hrs. CH₃ CN was removed under vacuo. The crude was extracted with AcOEt (3×200 ml), washed with water (50 ml) and with brine (50 ml). A purification by flash chromatography afforded the desired 2R-[3-(4-ethoxy-phenyl)-allyl]-3S-hydroxy-succinic acid diisopropyl ester (5.92 g, 84% yield).

¹H-NMR; delta (CDCl₃): 7.28 (2H, d, J=8.8 Hz), 6.83 (2H, d, J=8.8), 6.46 (1H, d, J=15.7 Hz), 6.02-6.12 (1H, m), 4.98-5.13 (2H, m), 4.26 (1H, dd, J=7.1, 3.0 Hz), 4.02 (2H, q, J=7.0 Hz): 3.23 (1H, d, J=7.1 Hz), 2.92-2.97 (1H, m), 2.68-2.79 (1H, m), 2.49-2.62 (1H, m), 1.41 (3H, t, J=7.0 Hz), 1.19-1.30 (12H, m).

LRMS: +ve ion 401 (M+Na).

Step C: 2R-[3-(4-ethoxy-phenyl)-propyl]-3S-hydroxy-succinic acid diisopropyl ester.

To a solution of 2R-[3-(4-ethoxy-phenyl)-allyl]-3S-hydroxy-succinic acid diisopropyl ester (129 mg, 0.34 mmol) in MeOH (10 ml) under an inert atmosphere, was added 10% Pd/C (13 mg). H₂ was bubbled through the resulting suspension for 30 min. The reaction mixture was then stirred under 1 atmosphere of H₂ for 16 hrs. Pd/C was filtered off and the solvent removed under reduced pressure to give 2R-[3-(4-ethoxy-phenyl)-propyl]-3S-hydroxy-succinic acid diisopropyl ester (115 mg, 88% yield).

¹H-NMR; delta (CDCl₃): 7.08 (2H, d, J=8.6 Hz), 6.81 (2H, d, J=8.6), 4.97-5.14 (2H, m), 4.20 (1H, dd, J=7.3, 3.5 Hz), 4.01 (2H, q, J=7.0 Hz), 3.18 (1H, d, J=7.3 Hz), 2.77-2.83 (1H, m), 2.55-2.62 (2H, m), 1.45-1.94 (4H, m), 1.40 (3H, t, J=7.0 Hz), 1.12-1.30 (12H, m).

LRMS: +ve ion xx (M+Na).

Step D: 2R-[3-(4-ethoxy-phenyl)-propyl]-3S-hydroxy-succinic acid.

To a solution of 2R-[3-(4-ethoxy-phenyl)-propyl]-3S-hydroxy-succinic acid diisopropyl ester (4.78 g, 12.6 mmol) in THF/water (3:1, 120 ml) was added NaOH (1.66 g, 41.5 mmol, 5.5 eq.). The reaction mixture was then stirred for 16 hrs at RT. The mixture was concentrated under reduced pressure and acidify to pH=3 by addition of HCl 1N. The hydroxy diacid was extracted with AcOEt. The organic layer was dried over MgSO₄ and the solvent removed under reduced pressure to give the desired 2R-[3-(4-ethoxy-phenyl)-propyl]-3S-hydroxy-succinic acid (3.66 g, 85% yield).

¹H-NMR; delta (MeOD): 7.07 (2H, d, J=8.6 Hz), 6.79 (2H, d, J=8.6), 4.23 (1H, d, J=5.8 Hz), 3.98 (2H, q, J=7.0 Hz), 2.76-2.81 (1H, m), 2.53-2.59 (2H, m), 1.55-1.72 (4H, m), 1.35 (3H, t, J=7.0 Hz).

LRMS: +ve ion 319 (M+Na); −ve ion 295 (M−H).

Step E: 2R-(2,2-dimethyl-5-oxo-[1,3]dioxolan-4S-yl)-5-(4-ethoxy-phenyl)-pentanoic acid.

To a solution of 2R-[3-(4-ethoxy-phenyl)-propyl]-3S-hydroxy-succinic acid (3.66 g, 12.3 mmol) in acetone (50 ml) under an inert atmosphere were added dimethoxy propane (2.58 ml, 21 mmol, 1.7 eq.) and copper chloride (165 mg, 1.2 mmol, 0.1 eq.). The reaction mixture was stirred at RT for 16 hrs. The solvent was then removed under vacuo to give 2R-(2,2-dimethyl-5-oxo-[1,3]dioxolan-4S-yl)-5-(4-ethoxy-phenyl)-pentanoic acid (4.03 g, 97% yield).

$^1$H-NMR; delta (CDCl$_3$): 7.08 (2H, d, J=8.5 Hz), 6.82 (2H, d, J=8.5), 4.48 (1H, d, J=4.8 Hz), 4.01 (2H, q, J=7.0 Hz), 2.91-2.98 (1H, m), 2.54-2.64 (3H, m), 1.23-2.20 (4H, m), 1.58 (3H, s), 1.53 (3H, s), 1.40 (3H, t, J=7.0 Hz).

LRMS: +ve ion 359 (M+Na); −ve ion 335 (M−H).

Step F. 2R-(2,2-dimethyl-5-oxo-[1,3]dioxolan-4S-yl)-5-(4-ethoxy-phenyl)-pentanoic acid pentafluorophenyl ester.

To a cold (0 C) solution of 2R-(2,2-dimethyl-5-oxo-[1,3]dioxolan-4S-yl)-5-(4-ethoxy-phenyl)-pentanoic acid (4.03 g, 12 mmol) and pentafluoro phenol (2.43 g, 13.2 mmol, 1.1 eq.) in CH$_2$ Cl$_2$ (50 ml) was added WSC (2.54 g, 13.2 mmol, 1.1 eq.). The reaction mixture was allowed to warm to RT overnight. CH$_2$Cl$_2$ was removed under vacuo and the resulting crude reaction mixture was dissolved in AcOEt (200 ml). The organic layer was washed with water (50 ml), NaHCO$_3$ sat (20 ml) and finally with brine (20 ml). Solvent was removed under reduced pressure to give an oil which was purified by flash chromatography to furnish the expected 2R-(2,2-dimethyl-5-oxo-[1,3]dioxolan-4S-yl)-5-(4-ethoxy-phenyl)-pentanoic acid pentafluorophenyl ester (3.94 g, 65% yield).

$^1$H-NMR; delta (CDCl$_3$): 7.09 (2H, d, J=8.4 Hz), 6.83 (2H, d, J=8.4 Hz), 4.56 (1H, d, J=6.0 Hz), 4.01 (2H, q, J=7.0 Hz), 3.20-3.28 (1H, m), 2.64 (2H, t, J=7.6 Hz), 1.98-2.08 (2H, m), 1.70-1.86 (2H, m), 1.62 (3H, s), 1.57 (3H, s), 1.40 (3H, t, J=7.0 Hz).

Step G. 5-{4-(4-Ethoxy-phenyl)-1-[4-(2-fluoro-phenyl)-piperazine-1-carbonyl]-butyl}-2,2-dimethyl-[1,3]dioxolan-4-one.

To a solution of 2R-(2,2-dimethyl-5-oxo-[1,3]dioxolan-4S-yl)-5-(4-ethoxy-phenyl)-pentanoic acid pentafluorophenyl ester (150 mg, 0.30 mmol) in CH$_2$ Cl$_2$ (10 ml) was added 1-(2-fluorophenyl)-4-piperazine (65 mg, 0.36 mmol, 1.2 eq.). The reaction mixture was stirred for 16 hrs and the solvent was removed under vacuo. The crude was taken-up in AcOEt (70 ml) and washed with water (10 ml), then with NaHCO$_3$ sat (10 ml) and finally with brine (10 ml). The solvent was dried over MgSO$_4$ and removed under reduced pressure to give the desired 5-{4-(4-Ethoxy-phenyl)-1-[4-(2-fluoro-phenyl)-piperazine-1-carbonyl]-butyl}-2,2-dimethyl-[1,3]dioxolan-4-one (97 mg, 65% yield.).

$^1$H-NMR; delta (CDCl$_3$):

Step H: 6-(4-ethoxy-phenyl)-3R-[4-(2-fluoro-phenyl)-piperazine-1-carbonyl]-2S-hydroxy-hexanoic acid methyl ester.

To a cold (0 C) solution of 5-{4-(4-ethoxy-phenyl)-1-[4-(2-fluoro-phenyl)-piperazine-1-carbonyl]-butyl}-2,2-dimethyl-[1,3]dioxolan-4-one (482 mg, 0.95 mmol) in methanol (5 ml) was added thionyl chloride (0.078 ml, 1.06 mmol, 1.1 eq.) dropwise. The reaction mixture was stirred to room temperature and then heated to reflux for 3 hours. The reaction mixture was then cooled to room temperature and evaporated under reduced pressure. The crude reaction was extracted with AcOEt (2×50 ml) and washed with 1M Na2 CO3 (50 ml) and brine (50 ml). The organic layer was dried over MgSO$_4$ and purification by flash chromatography gave the 6-(4-ethoxy-phenyl)-3R-[4-(2-fluoro-phenyl)-piperazine-1-carbonyl]-2S-hydroxy-hexanoic acid methyl ester as a colourless oil (200 mg, 44% yield).

$^1$H-NMR; delta (CDCl$_3$): 7.12 (2H, d, J=6.5 Hz), 7.08 (4H, m), 6.81 (2H, d, J=6.3 Hz), 5.00 (1H, d, J=6, 1 Hz), 3.98 (2H, q, 5.3, 8.9 Hz), 3.75 (3H, s), 3.40-3.65 (4H, m), 3.21 (1H, m), 2.99 (4H, bm), 2.64 (2H, m), 1.90-1.65 (4H, m), 1.45 (3H, m).

LRMS: +ve ion 473 (M+H).

Step I: 6-(4-ethoxy-phenyl)-3R-[4-(2-fluoro-phenyl)-piperazine-1-carbonyl]-2S-methoxy-hexanoic acid methyl ester To a cold solution (0 C) of 6-(4-ethoxy-phenyl)-3R-[4-(2-fluoro-phenyl)-piperazine-1-carbonyl]-2S-hydroxy-hexanoic acid methyl ester (200 mg, 0.44 mmol) in anhydrous DMF was added sodium hydride (20 mg, 0.48 mmol, 1.1 eq, 60% dispersion). The reaction mixture was stirred for 30 minutes before dropwise addition of methyl iodide (0.04 ml, 0.60 mmol, 1.2 eq). The reaction mixture was warmed to room temperature and stirred over 16 hours. The crude reaction was evaporated under reduced pressure and extracted with AcOEt (2×50 ml) and washed with water and brine (50 ml). Purification by flash chromatography afforded the desired 6-(4-ethoxy-phenyl)-3R-[4-(2-fluoro-phenyl)-piperazine-1-carbonyl]-2S-methoxy-hexanoic acid methyl ester as a colourless oil (125 mg, 61% yield).

$^1$H-NMR; delta (CDCl$_3$): 7.12 (2H, d, J=6.5 Hz), 7.08 (4H, m), 6.81 (2H, d, J=6.3 Hz), 5.00 (1H, d, J=6.1 Hz), 3.98 (2H, q, 5.3, 8.9 Hz), 3.75 (3H, s), 3.40-3.65 (4H, m), 3.30 (3H, s), 3.21 (1H, m), 3.05 (4H, bm), 2.64 (2H, m), 1.80-1.65 (4H, m), 1.39 (3H, t, J=7.0 Hz).

LRMS: +ve ion 487 (M+H).

Step J: 6-(4-ethoxy-phenyl)-3R-[4-(2-fluoro-phenyl)-piperazine-1-carbonyl]-2S-methoxy-hexanoic acid.

To a solution of 6-(4-ethoxy-phenyl)-3R-[4-(2-fluoro-phenyl)-piperazine-1-carbonyl]-2S-methoxy-hexanoic acid methyl ester (125 mg, 0.26 mmol) in methanol/water (3:1, 10 ml) was added NaOH (11 mg, 0.28 mmol, 1.1 eq.). The reaction mixture was then stirred for 16 hrs at RT. The mixture was concentrated under reduced pressure and acidified to pH=3 by addition of 1N HCl. The methoxy acid was extracted with AcOEt. The organic layer was dried over MgSO$_4$ and the solvent removed under reduced pressure to give the desired 6-(4-ethoxy-phenyl)-3R-[4-(2-fluoro-phenyl)-piperazine-1-carbonyl]-2S-methoxy-hexanoic acid (101 mg, 83% yield).

$^1$H-NMR; delta (CDCl$_3$): 7.12 (2H, d, J=6.5 Hz), 7.08 (4H, m), 6.81 (2H, d, J=6.3 Hz), 4.01 (1H, d, J=6.5 Hz), 3.98 (2H, m), 3.45 (3H, s), 3.30-2.85 (8H, m), 2.64 (2H, m), 1.80-1.65 (4H, m), 1.39 (3H, t, J=7.0 Hz).

LRMS: +ve ion 473.2 (M+H).

Step K: 6-(4-ethoxy-phenyl)-3R-[4-(2-fluoro-phenyl)-piperazine-1-carbonyl]-2S-hydroxy-hexanoic acid benzyloxy-amide.

To a cold solution (0 C) of 6-(4-ethoxy-phenyl)-3R-[4-(2-fluoro-phenyl)-piperazine-1-carbonyl]-2S-methoxy-hexanoic acid (101 mg, 0.21 mmol) in DMF (2 ml) was added benzylhydroxylamine (39 mg, 0.32 mmol), WSC (49 mg, 0.26 mmol) and finally HOBt (2 mg, 0.043 mmol). The reaction mixture was then allowed to warm to room temperature and stirred for 16 hrs. The solvent was removed under reduced pressure. The crude reaction was taken-up in AcOEt (30 ml) and washed with water (10 ml), then with NaHCO$_{3\ sat}$ (10 ml) and finally with brine (10 ml). The solvent was dried over MgSO$_4$ and removed under reduced pressure before purification by column chromatography to give the desired 6-(4-Ethoxy-phenyl)-3-[4-(2-fluoro-phenyl)-piperazine-1-carbonyl]-2-hydroxy-hexanoic acid benzyloxy-amide as a white solid (38 mg, 31% yield).

LRMS: +ve ion 578.2 (M+H).

Step L: 6-(4-ethoxy-phenyl)-3R-[4-(2-fluoro-phenyl)-piperazine-1-carbonyl]-2S-methoxy-hexanoic acid hydroxyamide.

To a solution of 6-(4-ethoxy-phenyl)-3R-[4-(2-fluoro-phenyl)-piperazine-1-carbonyl]-2S-hydroxy-hexanoic acid benzyloxy-amide (38 mg, 0.007 mmol) in MeOH (10 ml) under an inert atmosphere, was added 10% Pd/C (5 mg). H$_2$ was bubbled through the resulting suspension for 30 min. The reaction mixture was then stirred under 1 atmosphere of H$_2$ for 3 hrs. Pd/C was filtered off and the solvent removed under reduced pressure Purification by preparative HPLC gave 6-(4-ethoxy-phenyl)-3R-[4-(2-fluoro-phenyl)-piperazine-1-carbonyl]-2S-methoxy-hexanoic acid hydroxyamide as a white solid (5 mg, 40% yield).

Biological Results

A. Enzyme Inhibition Assays

Compounds of the invention were tested to assess their activities as inhibitors of MMP9, MMP12 and MMP-1.

MMP9 Assay Protocol

Compounds of the invention were tested for inhibitory activity against 92 kDa gelatinase (MMP9) in an assay using a coumarin-labelled peptide substrate, (7-methoxycoumarin-4-yl)acetyl-Pro-Leu-Gly-Leu-(3-[2,4-dinitrophenyl]-L-2,3-diaminopropionyl)-Ala-Arg-NH$_2$ (McaPLGLDpaAR) (Knight et al, FEBS Lett. 1992; 263-266).

Stock solutions were made up as follows:
Assay Buffer: 100 mM Tris-HCl pH 7.6 containing 100 mM NaCl, 10 mM CaCl$_2$, and 0.05% Brij 35
Substrate: 0.4 mM McaPLGLDpaAR (from Bachem) (0.437 mg/ml) stock solution in 100% DMSO (stored at −20° C.). Dilute to 8 µM in assay buffer.
Enzyme: Recombinant human 92 kDa gelatinase (MMP-9; APMA (4-aminophenylmercuric acetate)-activated if necessary) appropriately diluted in assay buffer.

Test Compounds were prepared initially as 10 mM compound solution in 100% DMSO, diluted to 1 mM in 100% DMSO, then serially diluted 3-fold in 100% DMSO across columns 1-10 of a 96-well microtitre plate Assay concentration range, 100 µM (column 1) to 5.1 nM (column 10)

The assay was performed in a total volume of 100 µl upper well in 96-well microtitre plates. Activated enzyme (20 µl) was added to the wells followed by 20 µl of assay buffer. Appropriate concentrations of test compounds dissolved in 10 µl of DMSO were then added followed by 50 µl of McaPLGLDpaAR (8 µM, prepared by dilution of DMSO stock in assay buffer). For each assay ten concentrations of test compound were examined in duplicate. Control wells lack either enzyme or test compound. The reactions were incubated at 37° C. for 2 hours. The fluorescence at 405 nm was measured immediately with an SLT Fluostar fluorometer (SLT Labinstruments GmbH, Grödig, Austria) using 320 nm excitation, without stopping the reaction.

The effect of the test compound was determined from the dose response curve generated by the 10 duplicate concentrations of inhibitor. The IC$_{50}$ (the concentration of compound required to give a 50% decrease in enzyme activity) was obtained by fitting data to the equation, $Y=a+((b-a)/(1+(c/X)^d))$. (Y=inhibition achieved for a particular dose; X=the dose in nM; a=minimum y or zero % inhibition; b=maximum y or 100% inhibition; c=is the IC$_{50}$; d=is the slope). The result was rounded to one significant figure.

MMP12 Assay Protocol

Compounds of the invention were tested for inhibitory activity against metalloelastase (MMP12) in an assay using a coumarin-labelled peptide substrate, (7-methoxycoumarin-4-yl)acetyl-Pro-Leu-Gly-Leu-(3-[2,4-dinitrophenyl]-L-2,3-diaminopropionyl)-Ala-Arg-NH$_2$ (McaPLGLDpaAR) (Knight et al, FEBS Lett. 1992; 263-266). The protocol for this assay was as described for the MMP9 assay above.

MMP1 Assay Protocol

Compounds of the invention were tested for inhibitory activity against collagenase (MMP1) in an assay using a coumarin-labelled peptide substrate, (7-methoxycoumarin-4-yl)acetyl-Pro-Leu-Gly-Leu-(3-[2,4-dinitrophenyl]-L-2,3-diaminopropionyl)-Ala-Arg-NH$_2$ (McaPLGLDpaAR) (Knight et al, FEBS Lett. 1992; 263-266). The protocol for this assay was as described for the MMP9 assay above.

Results:
Key to assay data

| Range | | |
|---|---|---|
| | A | <100 nM |
| | B | 100–1000 nM |
| | C | 1000–10,000 nM |
| | D | >10,000 nM |

For instance the inhibitory activities of some of the compounds of the examples against MMP-12, MMP-9, MMP-2 and MMP-1 are set out in the following table:

| Example Number | MMP-9 (nM) | MMP-2 (nM) | MMP-1 (nM) | MMP-12 (nM) |
|---|---|---|---|---|
| 4 | A | A | D | A |
| 5 | A | A | D | A |
| 6 | B | B | D | A |
| 12 | A | A | D | A |
| 13 | A | A | D | A |
| 14 | A | A | D | A |
| 20 | A | A | D | A |
| 62 | A | A | D | A |

B. Biological Assay: IL2-Induced Peritoneal Recruitment of Lymphocytes in Mice

Protocol

C3H Mice (Elevage Janvier) (8 week old, n=6) received IL2 (SPRI, 20 µg/kg, 40 ml/kg, ip) 15 min after administration of the test molecules. Twenty-four hours later, the animals were sacrificed and the lavage of the peritoneal cavity was conducted using 3×5 ml PBS-1 mM EDTA (+4° C.). After centrifugation (10 min at 3000 rpm), the pellet was resuspended in 1 ml PBS. The peritoneal cells were counted using a Beckman/Coulter counter. IL2 was solubilized in saline. The test compounds of the invention were solubilized or suspended in 0.5% carboxymethylcellulose (CMC)/0.25% Tween-20 and orally administered. Dexamethasone (0.1 mg/kg, po) was used as reference compound.

For instance, upon using the compounds of specified examples, the inhibition of IL-2 induced peritoneal recruitment was as set out in the following table:

| IL2-Induced peritoneal Recruitment | | | |
|---|---|---|---|
| | Doses (mg/kg) | Route | % Inhibition |
| Example 4 | 3 | po | 34% |
| Example 5 | 3 | po | 50% |
| Example 6 | 3 | po | 33% |
| Example 13 | 3 | po | 47% |
| Example 14 | 3 | po | 30% |
| Example 20 | 3 | po | 57% |
| Dexamethazone | 1 | sc | 76% |

The invention claimed is:

1. A compound of formula (I), or an enantiomer or diastereoisomer thereof, or a salt thereof:

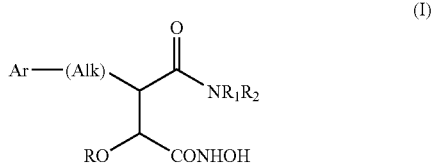

(I)

wherein Ar represents an phenyl optionally substituted by at least one substituent selected from $(C_1-C_3)$alkyl, $(C_1-C_3)$alkoxy, hydroxy, hydroxy$(C_1-C_3)$alkyl, mercapto, mercapto$(C_1-C_3)$alkyl, $(C_1-C_3)$alkylthio, halo, trifluoromethyl, trifluoromethoxy, nitro, nitrile (—CN), —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NHCOOR$^A$, —NR$^B$COOR$^A$, —NHSO$_2$OR$^A$, —NR$^B$SO$_2$OR$^A$, —NHCONH$_2$, —NR$^A$CONH$_2$, —NHCONHR$^B$, —NR$^A$CONHR$^B$, NHCONR$^A$R$^B$, or —NR$^A$CONR$^A$R$^B$ wherein R$^A$ and R$^B$ are independently $C_1-C_3$ alkyl, phenyl or a 5- or 6-membered monocyclic aryl or heteroaryl ring;

R represents hydrogen or $C_1-C_6$ alkyl, or $C_3-C_6$ cycloalkyl;

Alk represents a divalent $C_1-C_5$ alkylene or $C_2-C_5$ alkenylene radical; and $R_1$ and $R_2$ taken together with the nitrogen atom to which they are attached form a piperazinyl ring optionally substituted by at least one group of formula (II):

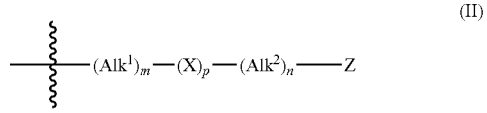

(II)

wherein m, p and n are independently 0 or 1;

Z represents, hydrogen, or an optionally substituted carbocyclic or heterocyclic ring of from 5 to 7 ring atoms which is optionally fused to another optionally substituted carbocyclic or heterocyclic ring of from 5 to 7 ring atoms;

Alk$^1$ and Alk$^2$ independently represent optionally substituted divalent $C_1-C_3$ alkylene radicals;

X represents —O—, —S—, —S(O)—, —S(O$_2$)—, —C(=O)—, —NH—, —NR$_3$—, —S(O$_2$)NH—, —S(O$_2$)NR$_3$—, —NHS(O$_2$)—, or —NR$_3$S(O$_2$)—, where R$_3$ is $C_1-C_3$ alkyl; and wherein, except for Ar defined above, optionally substituted means at least one substituent selected from $(C_1-C_6)$alkyl, $(C_1-C_6)$alkoxy, hydroxy, hydroxy$(C_1-C_6)$alkyl, mercapto, mercapto$(C_1-C_6)$alkyl, $(C_1-C_6)$alkylthio, halo, trifluoromethyl, trifluoromethoxy, nitro, nitrile (—CN), oxo, phenyl, —COOH, —COOR$^C$, —COR$^C$, —SO$_2$R$^C$, —CONH$_2$, —SO$_2$NH$_2$, —CONHR$^C$, —SO$_2$NHR$^C$, —CONR$^C$R$^D$, —SO$_2$NR$^C$R$^D$, —NH$_2$, —NHR$^C$, —NR$^C$R$^D$, —OCONH$_2$, —OCONHR$^C$, —OCONR$^C$R$^D$, —NHCOR$^C$, —NHCOOR$^C$, —NR$^D$COOR$^C$, —NHSO$_2$OR$^C$, —NR$^D$SO$_2$OR$^C$, —NHCONH$_2$, —NR$^C$CONH$_2$, —NHCONHR$^D$, —NR$^C$CONHR$^D$, —NHCONR$^C$R$^D$ or —NR$^C$CONR$^C$R$^D$ wherein R$^C$ and R$^D$ are independently a $(C_1-C_6)$alkyl or phenyl group.

2. A compound as claimed in claim 1 wherein R is hydrogen.

3. A compound as claimed in claim 1 wherein R is methyl.

4. A compound as claimed in claim 1 wherein R is ethyl, n-propyl, isopropyl, n-, sec- or tert-butyl, cyclopropyl, or cyclopentyl.

5. A compound as claimed in claim 1 wherein the phenyl ring is substituted in the 4- position.

6. A compound as claimed in claim 1 wherein Ar is substituted by at least one selected from methoxy, ethoxy, trifluoromethoxy, methyl, ethyl, trifluoromethyl, hydroxyl, mercapto, fluoro, chloro, and bromo.

7. A compound as claimed in claim 1 wherein Ar is 4-($C_1C_3$alkoxy)phenyl.

8. A compound as claimed in claim 1 wherein Ar is 4-ethoxyphenyl.

9. A compound as claimed in claim 1 wherein Alk is —CH$_2$—, —CH$_2$CH$_2$—, —CH$_2$CH(CH$_3$)—, —CH$_2$CH$_2$CH$_2$—, —CH$_2$CH$_2$CH$_2$CH$_2$—, —CH=CH—, —CH$_2$CH=CH—, —CH$_2$CH=CHCH$_2$—, or —CH=CHCH=CH—.

10. A compound as claimed in claim 1 wherein in the group (II), when present, p is 0, Z is hydrogen and at least one of n and m is 1.

11. A compound as claimed in claim 1 wherein in the group (II), when present, m, n and p are all 0 and Z is a carbocyclic or heterocyclic ring directly linked to a ring carbon or ring nitrogen of the —NR$_1$R$_2$ group.

12. A compound as claimed in claim 1 wherein in the group (II), when present, p is 0, at least one of m and n is 1, and Z is a carbocyclic or heterocyclic ring linked to a ring carbon or ring nitrogen of the —NR$_1$R$_2$ group via a $C_1-C_6$ alkylene linker between Z and the —NR$_1$R$_2$ ring.

13. A compound as claimed in claim 1 wherein in the group (II), when present, p is 1.

14. A compound as claimed in claim 1 of formula (1B) or (IC) or an enantiomer or diastereoisomer thereof, or a salt thereof:

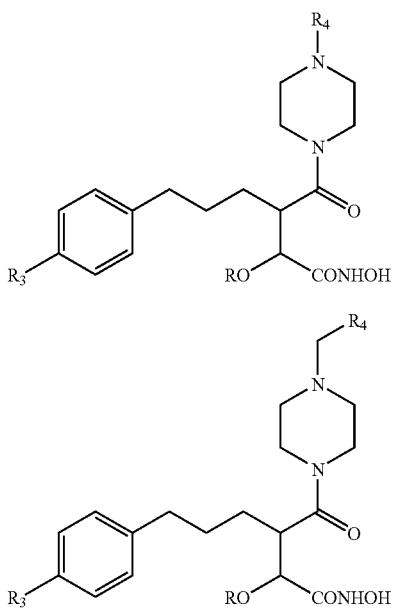

wherein R is hydrogen or methoxy, $R_3$ is trifluoromethyl, trifluoromethoxy $C_1$-$C_3$ alkoxy, hydroxy, or halo; $R_4$ is (i) —$SO_2R_5$ or —$COR_5$ wherein $R_5$ is $C_1$-$C_6$ alkyl or phenyl or monocyclic heteroaryl having 5 or 6 ring atoms, optionally substituted by ($C_1$-$C_3$)alkyl, ($C_1$-$C_3$) alkoxy, hydroxy, hydroxy($C_1$-$C_3$)alkyl, mercapto, mercapto($C_1$-$C_3$)alkyl, ($C_1$-$C_3$)alkylthio, halo, trifluoromethyl, trifluoromethoxy or (ii) phenyl or monocyclic heteroaryl having 5 or 6 ring atoms; optionally substituted by ($C_1$-$C_3$)alkyl, ($C_1$-$C_3$)alkoxy, hydroxy, hydroxy ($C_1$-$C_3$)alkyl, mercapto, mercapto($C_1$-$C_3$)alkyl, ($C_1$-$C_3$) alkylthio, halo, trifluoromethyl, trifluoromethoxy.

15. A compound as claimed in claim 14 wherein a heteroaryl ring forming part of $R_4$ is pyridyl, pyrimidinyl, triazinyl, thienyl, or furanyl.

16. A compound as claimed in claim 1 having the stereochemical configuration shown in formula (IA):

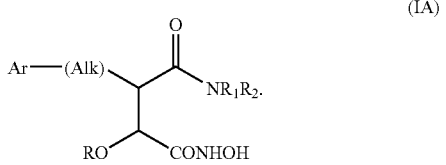

17. A compound as claimed in claim 1, which is selected from the group consisting of:

6-(4-ethoxy-phenyl)-2S-hydroxy-3R-[4-(3-methoxy-phenyl)-piperazine-1-carbonyl]-hexanoic acid hydroxyamide;

6-(4-ethoxy-phenyl)-2S-hydroxy-3R-[4-(4-methoxy-phenyl)-piperazine-1-carbonyl]-hexanoic acid hydroxyamide;

6-(4-ethoxy-phenyl)-2S-hydroxy-3R-(4-pyridin-2-yl-piperazine-1-carbonyl)hexanoic acid hydroxyamide;

6-(4-ethoxy-phenyl)-2S-hydroxy-3R-(4-pyridin-4-yl-piperazine-1-carbonyl)-hexanoic acid hydroxyamide;

3R-(4-benzo[1,3]dioxol-5-ylmethyl-piperazine-1-carbonyl)-6-(4-ethoxyphenyl)-2S-hydroxy-hexanoic acid hydroxyamide;

6-(4-ethoxy-phenyl)-2S-hydroxy-3R-(4-pyridin-4-ylmethyl-piperazine-1-carbonyl)-hexanoic acid hydroxyamide;

6-(4-ethoxy-phenyl)-2S-hydroxy-3R-(4-benzylpiperazine-1-carbonyl)-hexanoic acid hydroxyamide;

6-(4-ethoxy-phenyl)-2S-hydroxy-3R-(4-pyrimidin-2-yl-piperazine-1-carbonyl)-hexanoic acid hydroxyamide;

6-(4-ethoxy-phenyl)-2S-hydroxy-3R-[4-(4-trifluoromethyl-pyrimidin-2-yl)-piperazine-1-carbonyl]-hexanoic acid hydroxyamide;

6-(4-ethoxy-phenyl)-2S-hydroxy-3R-[4-(4-chloro-pyrimidin-2-yl)-piperazine-1-carbonyl]-hexanoic acid hydroxyamide;

3R-[4-(4,6-dimethoxy-[1,3,5]triazin-2-yl)-piperazine-1-carbonyl]-6-(4-ethoxyphenyl)-2S-hydroxy-hexanoic acid hydroxyamide;

6-(4-ethoxy-phenyl)-2S-hydroxy-3R-[4-(3-trifluoromethyl-phenyl)-piperazine-1-carbonyl]-hexanoic acid hydroxyamide;

6-(4-ethoxy-phenyl)-2S-hydroxy-3R-[4-(2-fluoro-phenyl)-piperazine-1-carbonyl]-hexanoic acid hydroxyamide;

3R-(4-benzyl-3RS-methyl-piperazine-1-carbonyl)-6-(4-ethoxy-phenyl)-2S hydroxy-hexanoic acid hydroxyamide;

3R-(3S-4-dibenzyl-piperazine-1-carbonyl)-6-(4-ethoxy-phenyl)-2S-hydroxyhexanoic acid hydroxyamide;

3R-(4-benzyl-3RS-phenyl-piperazine-1-carbonyl)-6-(4-ethoxy-phenyl)-2S-hydroxy-hexanoic acid hydroxyamide;

4-(4-benzo[1,3]dioxol-5-ylmethyl-piperazin-1-yl)-2S, N-dihydroxy-4-oxo-3R-(4 -trifluoromethoxy-benzyl)-butyramide;

4-(4-benzo[1,3]dioxol-5-ylmethyl-piperazin-1-yl)-3R-(4-benzyloxy-benzyl)2S, N-dihydroxy-4-oxo-butyramide;

6-(3,5-bis-trifluoromethyl-phenyl)-2S-hydroxy-3R-(4-pyridin-2-yl-piperazine-1-carbonyl)-hexanoic acid hydroxyamide;

3R-(2S-benzyl-4-methyl-piperazine-1-carbonyl)-6-(4-ethoxy-phenyJ)-2Shydroxy-hexanoic acid hydroxyamide;

6-(4-ethoxy-phenyl)-2S-hydroxy-3R-[4-(4-trifluoromethoxy-benzenesulfonyl)piperazine-1-carbonyl]-hexanoic acid hydroxyamide;

6-(4-ethoxy-phenyl)-2S-hydroxy-3R-[4-(toluene-4-sulfonyl)-piperazine-1-carbonyl]-hexanoic acid hydroxyamide;

3R-[4-(5-bromo-thiophene-2-sulfonyl)-piperazine-1-carbonyl]-6-(4-ethoxypheny1)-2S-hydroxy-hexanoic acid hydroxyamide;

3R-[4-(5-benzenesulfonyl-thiophene-2-sulfonyl)-piperazine-1-carbonyl]-6-(4-ethoxy-phenyl)-2S-hydroxy-hexanoic acid hydroxyamide;

3R-[4-(4-butoxy-benzenesulfonyl)-piperazine-1-carbonyl]-6-(4-ethoxy-phenyl)2S-hydroxy-hexanoic acid hydroxyamide;

6-(4-ethoxy-phenyl)-2S-hydroxy-3R-[4-(4-methoxy-2,3, 6-trimethylbenzenesulfonyl)-piperazine-1-carbonyl]-hexanoic acid hydroxyamide;

3R-[4-(3,4-dimethoxy-benzenesulfonyl)-piperazine-1-carbonyl]-6-(4-ethoxyphenyl)-2S-hydroxy-hexanoic acid hydroxyamide;

6-(4-methoxy-phenyl)-2S-hydroxy-3R-[4-(2-fluoro-phenyl)-piperazine-1carbonyl]-hexanoic acid hydroxyamide;

6-(4-methoxy-phenyl)-2S-hydroxy-3R-(4-pyridin-2-yl-piperazine-1-carbonyl)-hexanoic acid hydroxyamide;

6-(4-fluoro-phenyl)-3R-[4-(2-fluoro-phenyl)-piperazine-1-carbonyl]-2S-hydroxy-hexanoic acid hydroxyamide;

6-(4-fluoro-phenyl)-2S-hydroxy-3R-(4-pyridin-2-yl-piperazine-1-carbonyl)-hexanoic acid hydroxyamide;

3R-(4-benzyl-2S-methyl-piperazine-1-carbonyl)-6-(4-ethoxy-phenyl)-2S-hydroxy-hexanoic acid hydroxyamide;

3R-(4-benzyl-2S-methyl-piperazine-1-carbonyl)-6-(4-methoxy-phenyl)-2S-hydroxy-hexanoic acid hydroxyamide;

3R-(4-benzyl-2S-i-butyl-piperazine-1-carbonyl)-6-(4-methoxy-phenyl)-2S-hydroxy-hexanoic acid hydroxyamide;

3R-(4-benzyl-2S-methyl-piperazine-1-carbonyl)-6-(4-fluoro-phenyl)-2S-hydroxy-hexanoic acid hydroxyamide;

3R-(4-benzyl-2S-i-butyl-piperazine-1-carbonyl)-6-(4-fluoro-phenyl)-2S-hydroxy-hexanoic acid hydroxyamide;

4-[5-(4-ethoxy-phenyl)-2R-(1S-hydroxy-hydroxycarbamoyl-methyl)-pentanoyl]-2S-methyl-piperazine-1-carboxylic acid tert-butyl ester;

4-[5-(4-ethoxy-phenyl)-2R-(1S-hydroxy-hydroxycarbamoyl-methyl)-pentanoy1]-2S-i-butyl-piperazine-1-carboxylic acid tert-butyl ester;

4-[5-(4-methoxy-phenyl)-2R-(1S-hydroxy-hydroxycarbamoyl-methyl)-pentanoyl]-2S-methyl-piperazine-1-carboxylic acid tert-butyl ester;

4-[5-(4-methoxy-phenyl)-2R-(1S-hydroxy-hydroxycarbamoyl-methyl)-pentanoyl]-2S-i-butyl-piperazine-1-carboxylic acid tert-butyl ester;

4-[5-(4-fluoro-phenyl)-2R-(1S-hydroxy-hydroxycarbamoyl-methyl)-pentanoyl]-2S-methyl-piperazine-1-carboxylic acid tert-butyl ester;

4-[5-(4-fluoro-phenyl)-2R-(1S-hydroxy-hydroxycarbamoyl-methyl)-pentanoyl]-2S-i-butyl-piperazine-1-carboxylic acid tert-butyl ester; and 6-(4-ethoxy-phenyl)-2S-methoxy-3R-[4-(2-fluoro-phenyl)-piperazine-1carbonyl]-hexanoic acid hydroxyamide.

18. A pharmaceutical composition comprising a compound as claimed in claim 1, together with a pharmaceutically acceptable carrier.

19. A method of treating arthritis, wherein the arthritis is selected from rheumatoid arthritis, septic arthritis, osteoarthritis, or psoriatic arthritis, in mammals, which method comprises administering to the mammal an effective amount of a compound as claimed in claim 1.

* * * * *